US010660874B2

(12) United States Patent
Bugni et al.

(10) Patent No.: US 10,660,874 B2
(45) Date of Patent: May 26, 2020

(54) ECTEINAMYCIN, COMPOSITIONS AND USES THEREOF

(71) Applicant: Wisconsin Alumni Research Foundation, Madison, WI (US)

(72) Inventors: Timothy Scott Bugni, Madison, WI (US); Thomas Philip Wyche, Chelsea, MA (US); Douglas R. Braun, Mount Horeb, WI (US); Jeffrey S. Piotrowski, Madison, WI (US); Nasia Safdar, Madison, WI (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 0 days.

(21) Appl. No.: 15/522,713

(22) PCT Filed: Oct. 28, 2015

(86) PCT No.: PCT/US2015/057865
§ 371 (c)(1),
(2) Date: Apr. 27, 2017

(87) PCT Pub. No.: WO2016/069776
PCT Pub. Date: May 6, 2016

(65) Prior Publication Data
US 2017/0348278 A1    Dec. 7, 2017

Related U.S. Application Data

(60) Provisional application No. 62/069,652, filed on Oct. 28, 2014.

(51) Int. Cl.
*A61K 31/365* (2006.01)
*A61K 45/06* (2006.01)

(52) U.S. Cl.
CPC ............ *A61K 31/365* (2013.01); *A61K 45/06* (2013.01)

(58) Field of Classification Search
CPC ........ A61K 31/365; A61K 45/06; A61P 31/04
USPC ....................................................... 514/473
See application file for complete search history.

(56) References Cited

U.S. PATENT DOCUMENTS 4,407,946 A    10/1983    Labeda et al.

OTHER PUBLICATIONS

Wyche et al. (AN 2014:587869 BIOSIS, DN PREV201400587869, Planta Medica, (Jul. 2013) vol. 79, No. 10, pp. 822, http://www.thieme.de/plantamedica/index.html. meeting Info.: Annual Meeting of the American-Society-of-Pharmacognosy. St. Louis, MO, USA. Jul. 14-17, 2013. Amer Soc Pharmacognosy).*
Bastin et al. (Organic Process Research & Development 2000, 4, 427-435).*
Wyche et al. (ACS Chem Biol. (2017, 12, pp. 2287-2295, Chemical Genome, Structure Elucidation and in Vivo Studies of the Marine-Derived Anticlostridial Ecteinamycin).*
Bugni, T. et al.; 2014 Pilot Awards; Novel Therapeutic Pilot Awards Ecteinamycin as Therapeutic for Treatment of Clostridium difficile; University of Wisconsin ICTR Today Newsletters; Sep. 1, 2014; http//scbrm.bme.wisc.edu/documents/ICTR_Today_v7n4_vba.pdf (6 pages).
Cornilescu, G. et al; "An Rdc Based Force Field Method to Solve the Chiral Configuration of Complex Natural and Synthetic Products"; EUROMAR 2015 Program and Abstract Book; Jul. 5, 2015, pp. 453-454.
Fung et al, S.E. ACS Chem. Biol. 2014, 9, 247-257.
International Search Report and Written Opinion for PCT/US/057865 dated Dec. 2, 2015 (13 pages).
Wyche T. et al; "Structure Elucidation and Therapeutic Potential of Three Novel Classes of Natural Products from an Dscidian-Derived *Actinomadura* sp"; Jul. 16, 2013 (45 pages).
Wyche T. et al; "Structure Elucidation and Therapeutic Potential of Three Novel Classes of Natural Products from an Dscidian-Derived *Actinomadura* sp"; Planta Medica; vol. 79; No. 10; Jul. 14, 2013 (1 page) p. CL12.
Wyche, T et al., "First Natural Analogs of the Cytotoxic Thiodepsipeptide Thiocoraline A from a Marine *Verrucosispora* sp.," J. Org. Chem., (Aug. 19, 2011), vol. 76, No. 16, pp. 6542-6547.

* cited by examiner

*Primary Examiner* — Sabiha N Qazi
(74) *Attorney, Agent, or Firm* — Foley & Lardner LLP

(57) ABSTRACT

An isolated or synthesized compound of Formula I and salts thereof are provided. A compound isolated from *Actinomadura* and having a chemical formula of $C_{38}H_{60}O_{12}$ is also provided. Compositions including the compounds and methods of using the compounds to treat bacterial infections including gram positive infections such as *C. difficile* are also disclosed.

(I)

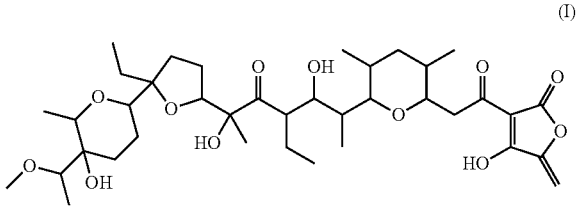

19 Claims, 9 Drawing Sheets

ECTEINAMYCIN, COMPOSITIONS AND USES THEREOF

CROSS-REFERENCE TO RELATED PATENT APPLICATIONS

This application is a U.S. National Phase Application under 35 U.S.C. § 371 of International Application No. PCT/US2015/057865, filed on Oct. 28, 2015, which claims priority to U.S. Provisional Patent Application No. 62/069,652, filed Oct. 28, 2014, the entire disclosure of which is hereby incorporated by reference in its entirety for any and all purposes.

STATEMENT OF GOVERNMENT SUPPORT

This invention was made with government support under GM092009 and GM104195 awarded by the National Institutes of Health and DE-FC02-07ER64494 awarded by the US Department of Energy. The government has certain rights in the invention.

FIELD OF THE TECHNOLOGY

The present technology relates to a new class of compounds called Ecteinamycin, compositions and methods of use thereof. Specifically, new isolated compounds useful as antibacterials are disclosed herein.

SUMMARY

A new compound, called ecteinamycin has been discovered and isolated from *Actinomadura*, a bacterium collected from a species of sea squirt. Ecteinamycin has the chemical formula $C_{38}H_{60}O_{12}$. Isolated ecteinamycin exhibits $^{13}C$ NMR peaks at about 183.3 ppm and about 89.7 ppm and $^1H$ NMR peaks at about 4.77 ppm and about 5.16 ppm. It may further exhibit $^{13}C$ NMR peaks at about 73.2 ppm, about 78.9 ppm, about 89.1 ppm, about 97.1 ppm, about 153.3 ppm, about 171.3 ppm, about 199.8 ppm, and about 222.9 ppm. Ecteinamycin may exhibit one or more IR bands at about 1735, about 1635, about 1538, about 1457, or about 1215 cm$^{-1}$. Ecteinamycin may also exhibit one or more UV $\lambda_{max}$ at about 200, about 250, or about 299 nm. Pharmaceutical compositions including ecteinamycin (or pharmaceutically acceptable salts thereof) and a pharmaceutically acceptable carrier are provided. Methods of treating bacterial infections by administering ecteinamycin to a mammal in need thereof are disclosed.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

Figure 1:
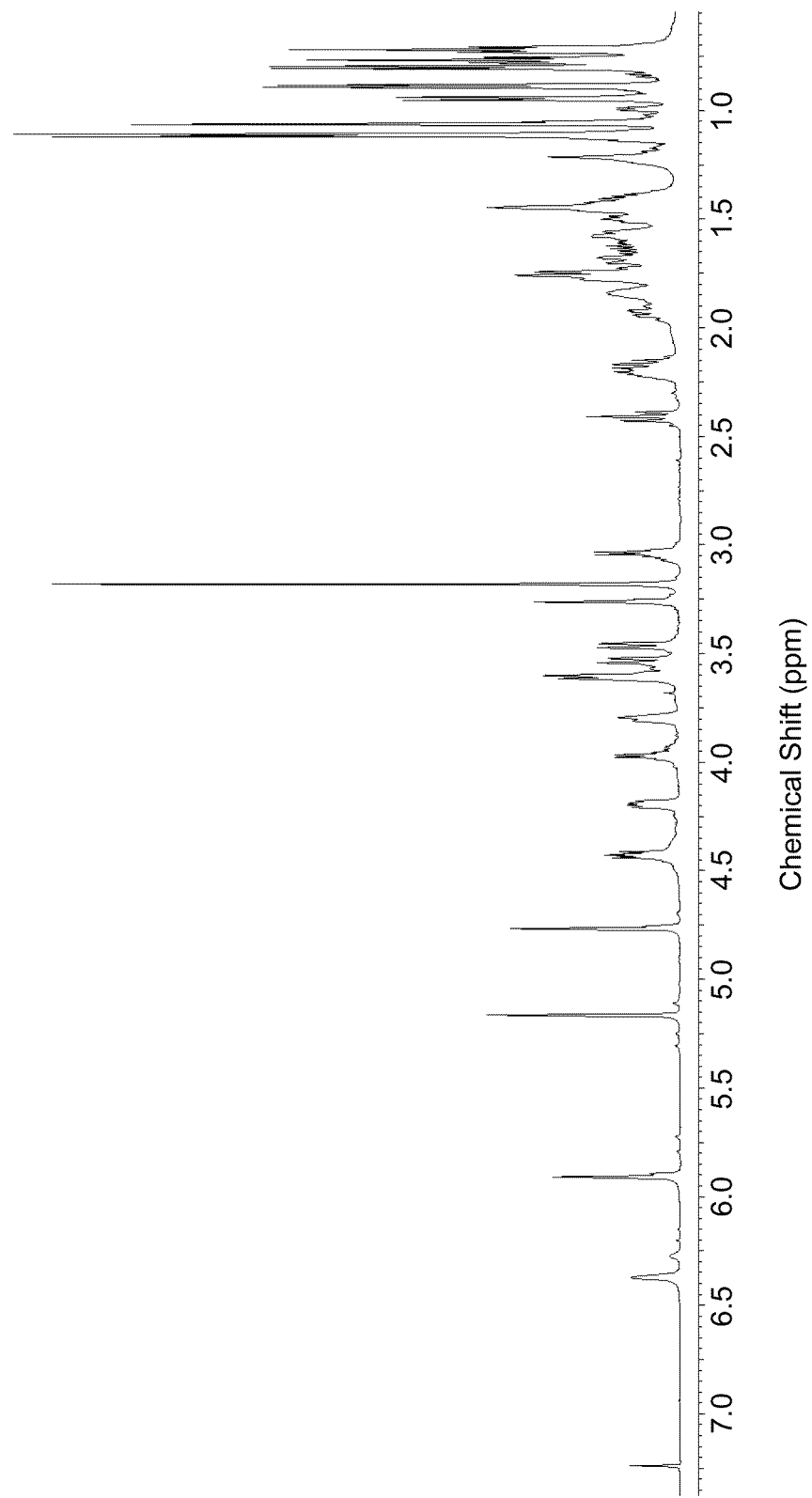
FIG. 1 shows a $^1H$ NMR (600 MHz, CDCl$_3$) spectrum of ecteinamycin.
Figure 2:
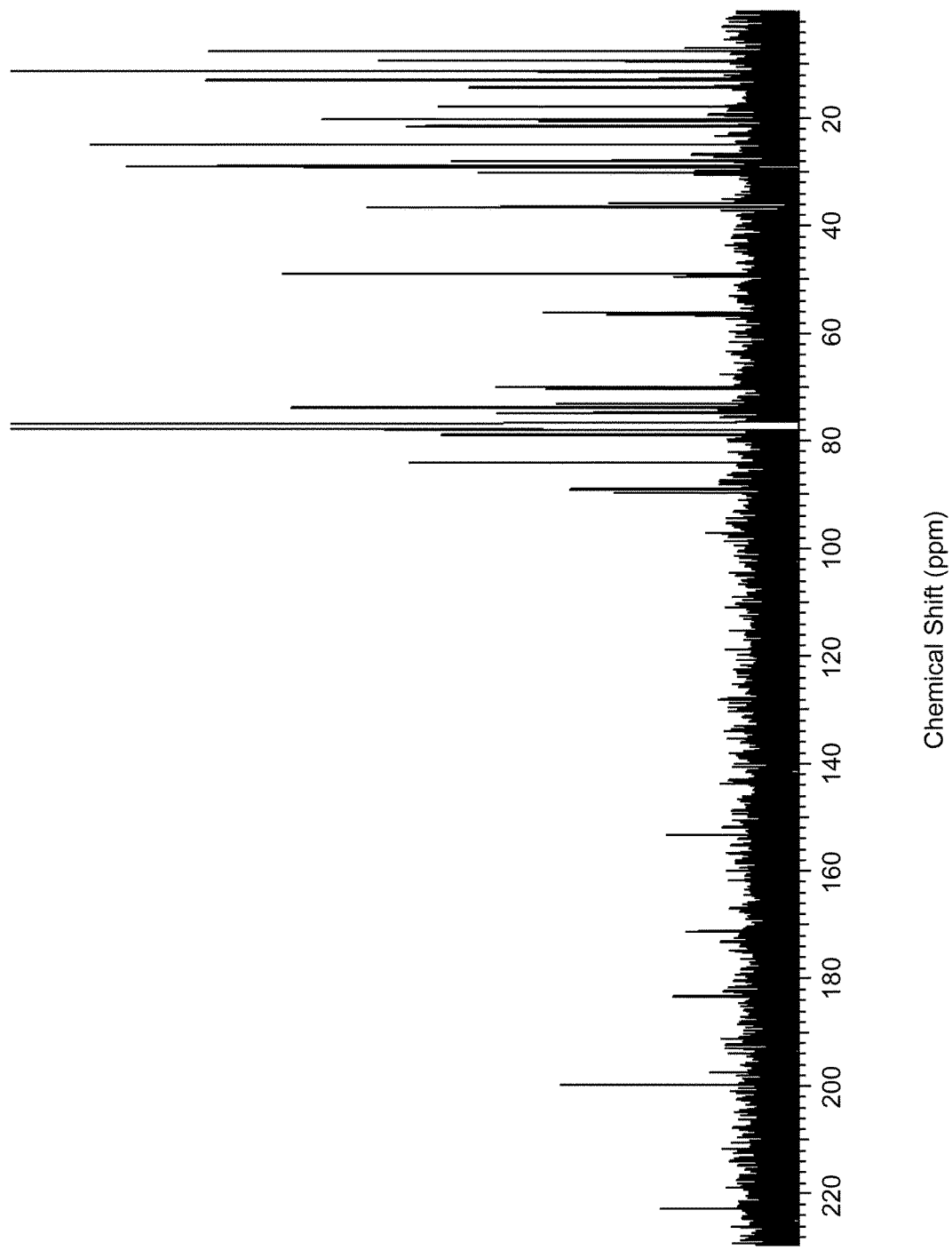
FIG. 2 shows a $^{13}C$ NMR (125 MHz, CDCl$_3$) spectrum of ecteinamycin.
Figure 3:
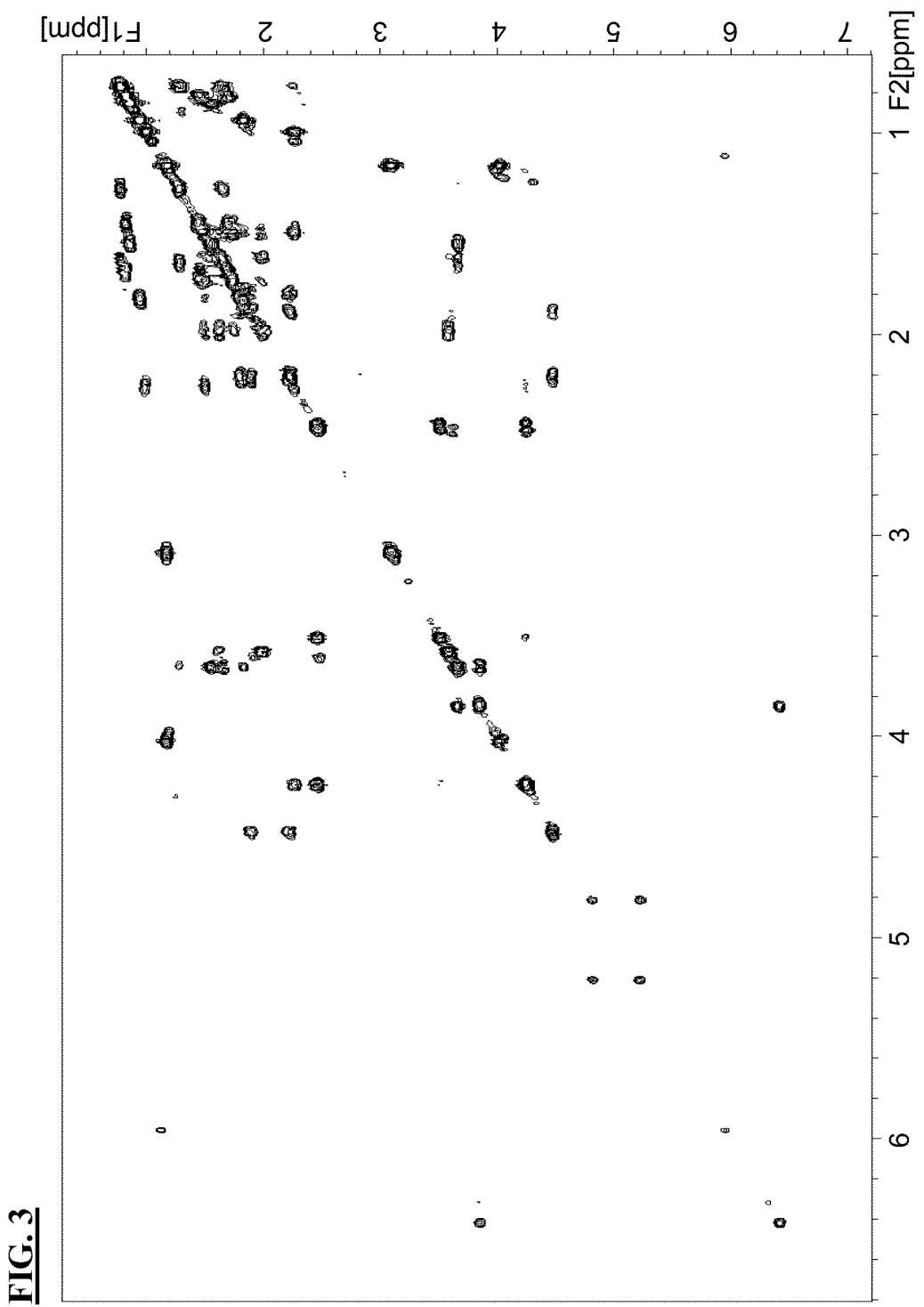
FIG. 3 shows a gCOSY (600 MHz, CDCl$_3$) spectrum of ecteinamycin.
Figure 4:
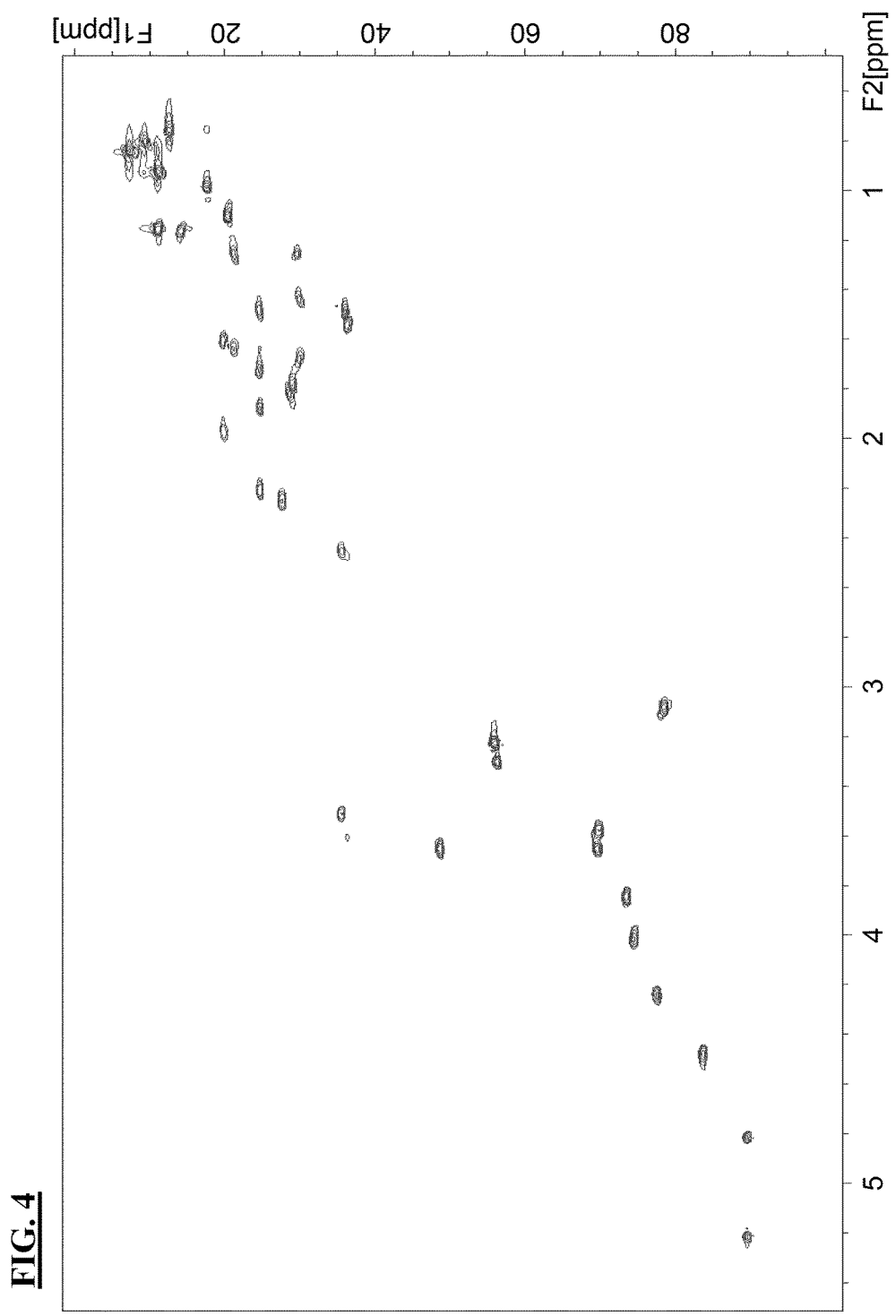
FIG. 4 shows a gHSQC (600 MHz, CDCl$_3$) spectrum of ecteinamycin.
Figure 5:
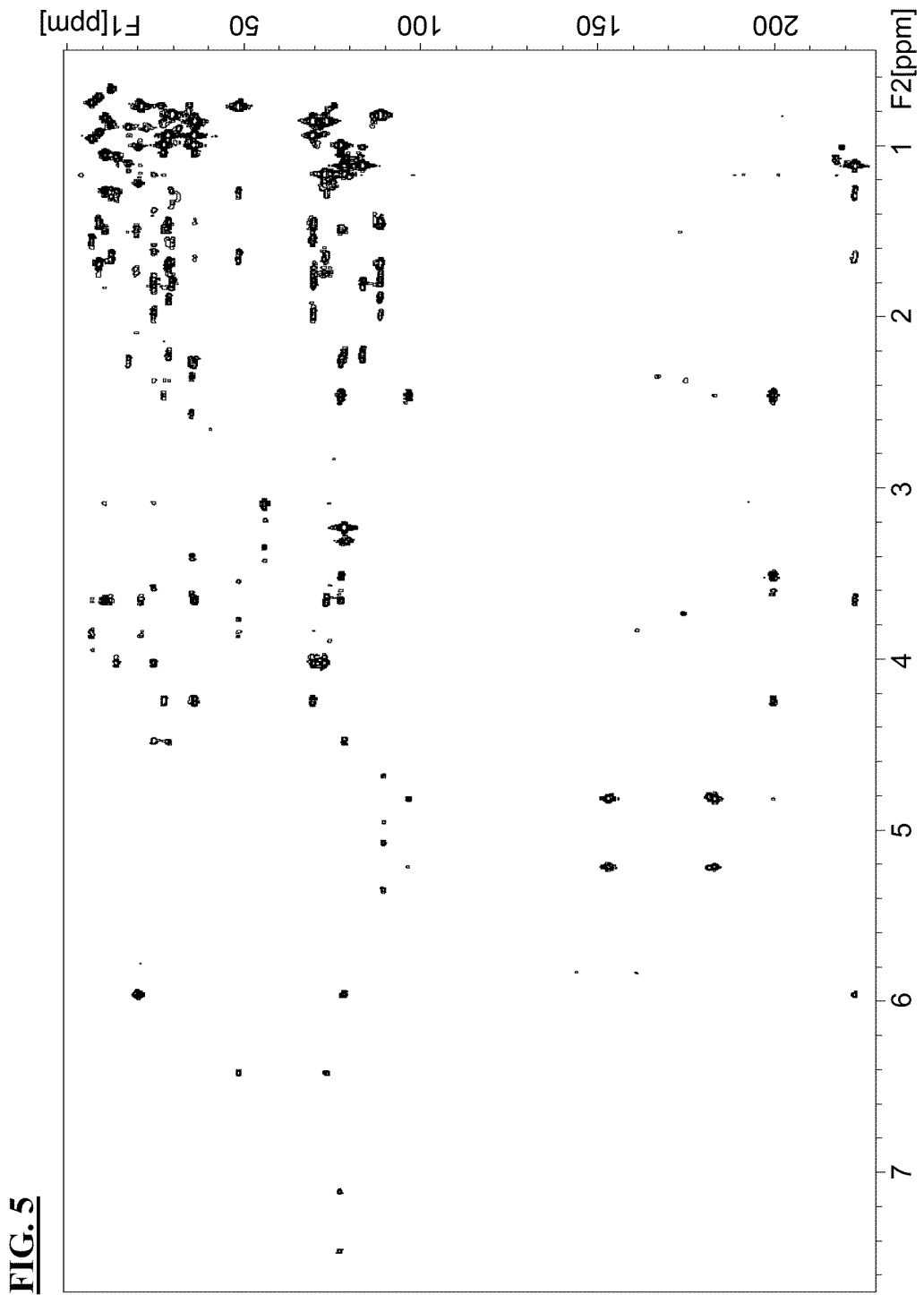
FIG. 5 shows a gHMBC (600 MHz, CDCl$_3$) spectrum of ecteinamycin.
Figure 6:
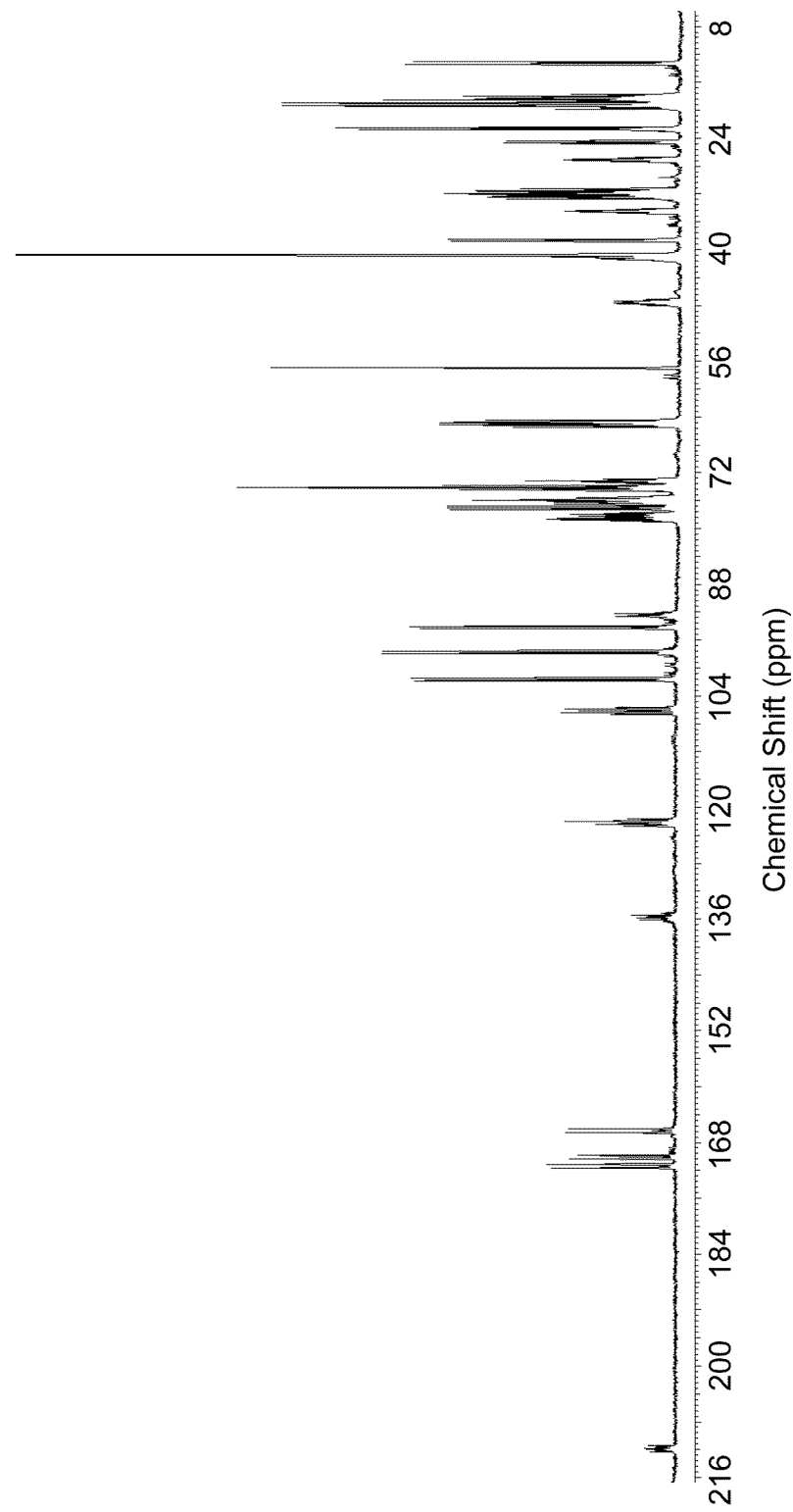
FIG. 6 shows a $^{13}C$ NMR (125 MHz, CDCl$_3$) spectrum of ($^{13}C$-labeled) ecteinamycin.
Figure 7:
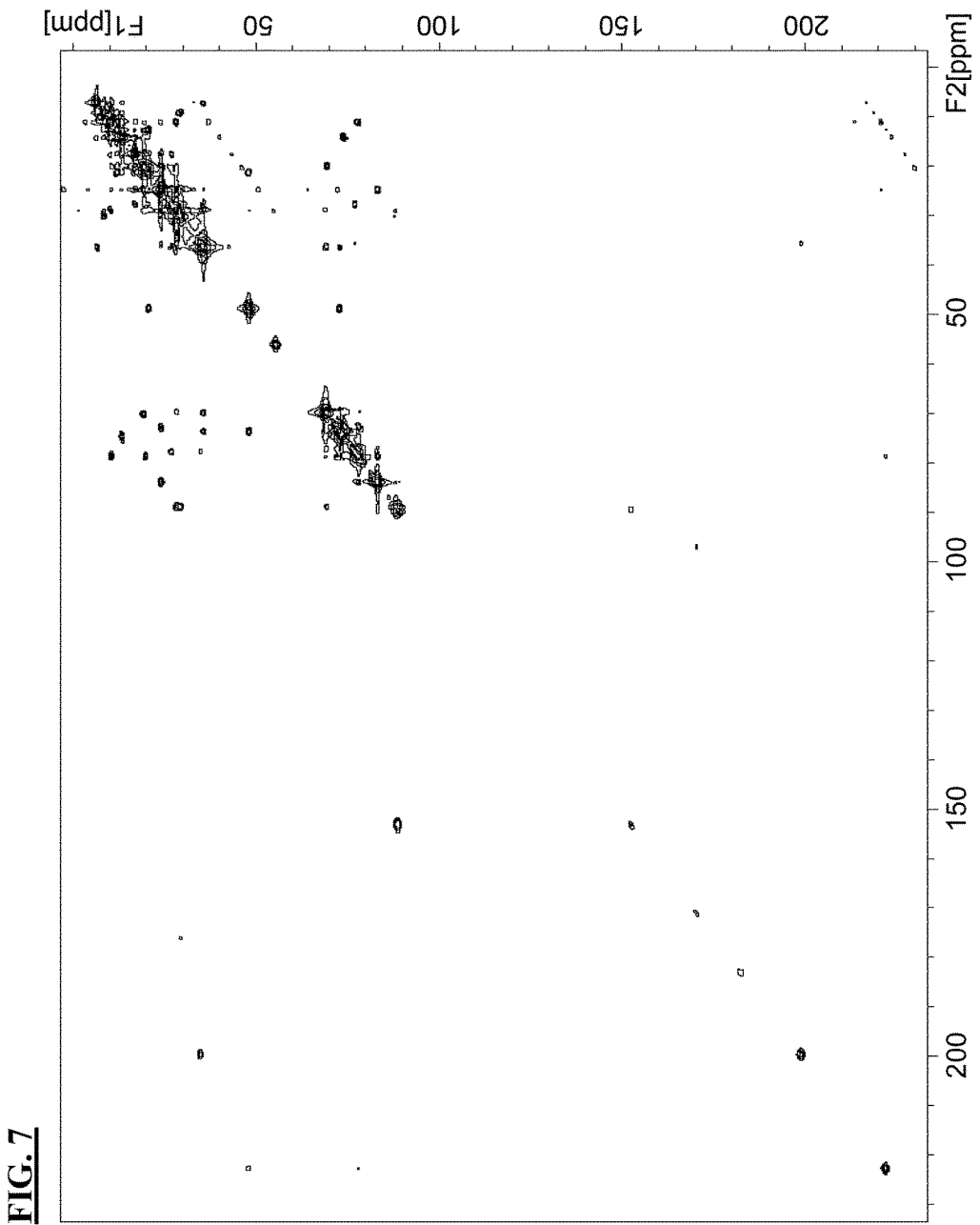
FIG. 7 shows a $^{13}C$-$^{13}C$ COSY (125 MHz, CDCl$_3$) spectrum of ($^{13}C$-labeled) ecteinamycin.

The present technology provides an isolated or synthesized compound useful for the treatment of bacterial infections. Thus, in accordance with one aspect, the technology includes a compound isolated from *Actinomadura* and having a chemical formula of $C_{38}H_{60}O_{12}$ and salts thereof, including but not limited to, pharmaceutical salts thereof.

The present technology further provides an isolated compound having a chemical formula of $C_{38}H_{60}O_{12}$ (and salts thereof) and may exhibit $^{13}C$ NMR peaks at about 183.3 ppm and about 89.7 ppm and $^1H$ NMR peaks at about 4.77 ppm and about 5.16 ppm. The isolated compound may further exhibit $^{13}C$ NMR peaks at about 73.2 ppm, about 78.9 ppm, about 89.1 ppm, about 97.1 ppm, about 153.3 ppm, about 171.3 ppm, about 199.8 ppm, and about 222.9 ppm. The isolated compound may exhibit any of the $^{13}C$ and $^1H$ NMR peaks listed in Table 3 in Example 2, herein. The isolated compound having a chemical formula of $C_{38}H_{60}O_{12}$ (and salts thereof) may exhibit one or more IR bands at about 1735, about 1635, about 1538, about 1457, or about 1215 cm$^{-1}$. The term "about" will be understood by those of skill in the art to include values within ±2% of the stated value, or in some embodiments, ±1% or even ±0.5% of the stated values.

In any embodiment described herein, the present technology provides an isolated or synthesized compound of Formula I:

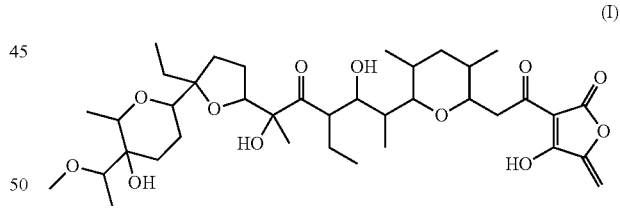

(I)

and salts thereof. A compound of Formula I may be numbered as indicated below, and such numbering is referred to herein.

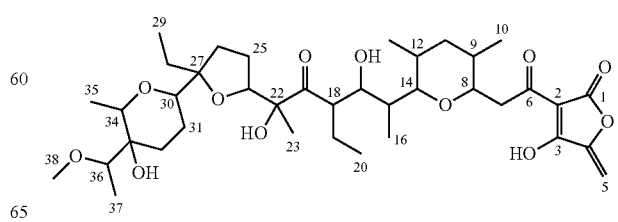

The compounds described herein may be isolated at various purities, e.g., a purity of at least 60 wt %, at least 70 wt %, at least 80 wt %, at least 90 wt %, at least 95 wt %, at least 96, at least 97 wt %, at least 98 wt %, at least 99 wt % or at least 99.5 wt %.

Those of skill in the art will appreciate that compounds of the present technology may exhibit the phenomena of tautomerism, conformational isomerism, geometric isomerism and/or stereoisomerism. As the formula drawings within the specification and claims can represent only one of the possible tautomeric, conformational isomeric, stereoisomeric or geometric isomeric forms, it should be understood that the technology encompasses any tautomeric, conformational isomeric, stereoisomeric and/or geometric isomeric forms of the compounds having one or more of the utilities described herein, as well as mixtures of these various different forms.

Stereoisomers of compounds (also known as optical isomers) include all chiral, diastereomeric, and racemic forms of a structure, unless the specific stereochemistry is expressly indicated. Thus, compounds disclosed herein include enriched or resolved optical isomers at any or all asymmetric atoms as are apparent from the depictions. Both racemic and diastereomeric mixtures, as well as the individual optical isomers can be isolated or synthesized so as to be substantially free of their enantiomeric or diastereomeric partners, and these stereoisomers are all within the scope of the present technology.

Ecteinamycin includes 14 chiral centers. The isolated compound (and salts thereof) may be in accordance with Formula IA:

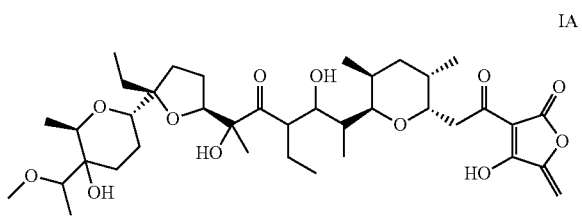 [SMILES: C=C1OC(=O)C(C(=O)C[C@@H]2O[C@@H](C(C)C(O)C(CC)C(=O)C(C)(O)[C@@H]3CC[C@@](CC)([C@@H]4CCC(O)(C(C)OC)[C@@H](C)O4)O3)[C@@H](C)C[C@@H]2C)=C1O]

IA

The compound of Formula IA may have the configuration at C15, C17, C18, C22, C33 and C36 as shown in at least one row of Table 1.

The compound of Formula I (and salts thereof) may have the configuration at C8, C9, C12, and C14, as shown in at least one row of Table 2.

TABLE 1

| Row No. | C15 | C17 | C18 | C22 | C33 | C36 |
|---|---|---|---|---|---|---|
| 1 | R | R | R | R | R | R |
| 2 | R | R | R | R | R | S |
| 3 | R | R | R | R | S | R |
| 4 | R | R | R | S | R | R |
| 5 | R | R | S | R | R | R |
| 6 | R | S | R | R | R | R |
| 7 | S | R | R | R | R | R |
| 8 | R | R | R | R | S | S |
| 9 | R | R | R | S | R | S |
| 10 | R | R | S | R | R | S |
| 11 | R | S | R | R | R | S |
| 12 | S | R | R | R | R | S |
| 13 | R | R | R | S | S | R |
| 14 | R | R | S | R | S | R |
| 15 | R | S | R | R | S | R |
| 16 | S | R | R | R | S | R |
| 17 | R | R | S | S | R | R |
| 18 | R | S | R | S | R | R |
| 19 | S | R | R | S | R | R |
| 20 | R | S | S | R | R | R |
| 21 | S | R | S | R | R | R |
| 22 | S | S | R | R | R | R |
| 23 | R | R | R | S | S | S |
| 24 | R | R | S | R | S | S |
| 25 | R | S | R | R | S | S |
| 26 | S | R | R | R | S | S |
| 27 | R | R | S | S | R | S |
| 28 | R | R | S | S | R | S |
| 29 | S | R | R | S | R | S |
| 30 | R | S | S | R | R | S |
| 31 | S | R | S | R | R | S |
| 32 | S | S | R | R | R | S |
| 33 | S | S | R | R | S | R |
| 34 | S | S | R | S | R | R |
| 35 | S | S | S | R | R | R |
| 36 | R | R | S | S | S | R |
| 37 | R | S | R | S | S | R |
| 38 | S | R | R | S | S | R |
| 39 | R | S | S | R | S | R |
| 40 | S | R | S | R | S | R |
| 41 | R | S | S | S | R | R |
| 42 | S | R | S | S | R | R |
| 43 | R | R | S | S | S | S |
| 44 | R | S | R | S | S | S |
| 45 | S | R | R | S | S | S |
| 46 | R | S | S | R | S | S |
| 47 | S | R | S | R | S | S |
| 48 | S | S | R | R | S | S |
| 49 | R | S | S | S | R | S |
| 50 | S | R | S | S | R | S |
| 51 | S | S | R | S | R | S |
| 52 | S | S | S | R | R | S |
| 53 | S | S | S | S | R | R |
| 54 | R | S | S | S | S | R |
| 55 | S | S | S | R | S | R |
| 56 | S | S | R | S | S | R |
| 57 | S | R | S | S | S | R |
| 58 | R | S | S | S | S | S |
| 59 | S | S | S | S | R | S |
| 60 | S | S | S | R | S | S |
| 61 | S | S | R | S | S | S |
| 62 | S | R | S | S | S | S |
| 63 | S | S | S | S | S | R |
| 64 | S | S | S | S | S | S |

TABLE 2

| Row No. | C8 | C9 | C12 | C14 |
|---|---|---|---|---|
| 1 | R | R | R | R |
| 2 | R | R | R | S |
| 3 | R | R | S | R |
| 4 | R | S | R | S |
| 5 | S | R | R | R |
| 6 | R | R | S | S |
| 7 | R | S | R | S |
| 8 | S | R | R | S |
| 9 | S | R | S | R |
| 10 | S | S | R | R |
| 11 | S | S | S | R |
| 12 | S | S | R | S |
| 13 | S | R | S | S |
| 14 | R | S | S | S |
| 15 | S | S | S | S |

The compound of any one row of Table 2 may further have the configuration at C15, C17, C18, C22, C33 and C36 as shown in at least one row of Table 3.

TABLE 3

| Row No. | C15 | C17 | C18 | C22 | C33 | C36 |
|---|---|---|---|---|---|---|
| 1 | R | R | R | R | R | R |
| 2 | R | R | R | R | R | S |
| 3 | R | R | R | R | S | R |
| 4 | R | R | R | S | R | R |
| 5 | R | R | S | R | R | R |
| 6 | R | S | R | R | R | R |
| 7 | S | R | R | R | R | R |
| 8 | R | R | R | R | S | S |
| 9 | R | R | R | S | R | S |
| 10 | R | R | S | R | R | S |
| 11 | R | S | R | R | R | S |
| 12 | S | R | R | R | R | S |
| 13 | R | R | R | S | S | R |
| 14 | R | R | S | R | S | R |
| 15 | R | S | R | R | S | R |
| 16 | S | R | R | R | S | R |
| 17 | R | R | S | S | R | R |
| 18 | R | S | R | S | R | R |
| 19 | S | R | R | S | R | R |
| 20 | R | S | S | R | R | R |
| 21 | S | R | S | R | R | R |
| 22 | S | S | R | R | R | R |
| 23 | R | R | R | S | S | S |
| 24 | R | R | S | R | S | S |
| 25 | R | S | R | R | S | S |
| 26 | S | R | R | R | S | S |
| 27 | R | R | S | S | R | S |
| 28 | R | S | R | S | R | S |
| 29 | S | R | R | S | R | S |
| 30 | R | S | S | R | R | S |
| 31 | S | R | S | R | R | S |
| 32 | S | S | R | R | R | S |
| 33 | S | S | R | R | S | R |
| 34 | S | S | R | S | R | R |
| 35 | S | S | S | R | R | R |
| 36 | R | R | S | S | S | R |
| 37 | R | S | R | S | S | R |
| 38 | S | R | R | S | S | R |
| 39 | R | S | S | R | S | R |
| 40 | S | R | S | R | S | R |
| 41 | R | S | S | S | R | R |
| 42 | S | R | S | S | R | R |
| 43 | R | R | S | S | S | S |
| 44 | R | S | R | S | S | S |
| 45 | S | R | R | S | S | S |
| 46 | R | S | S | R | S | S |
| 47 | S | R | S | R | S | S |
| 48 | S | S | R | R | S | S |
| 49 | R | S | S | S | R | S |
| 50 | S | R | S | S | R | S |
| 51 | S | S | R | S | R | S |
| 52 | S | S | S | R | R | S |
| 53 | S | S | S | S | R | R |
| 54 | R | S | S | S | S | R |
| 55 | S | S | S | R | S | R |
| 56 | S | S | R | S | S | R |
| 57 | S | R | S | S | S | R |
| 58 | R | S | S | S | S | S |
| 59 | S | S | S | S | R | S |
| 60 | S | S | S | R | S | S |
| 61 | S | S | R | S | S | S |
| 62 | S | R | S | S | S | S |
| 63 | S | S | S | S | S | R |
| 64 | S | S | S | S | S | S |

The isolated compound (and salts thereof) may be in accordance with Formula IB:

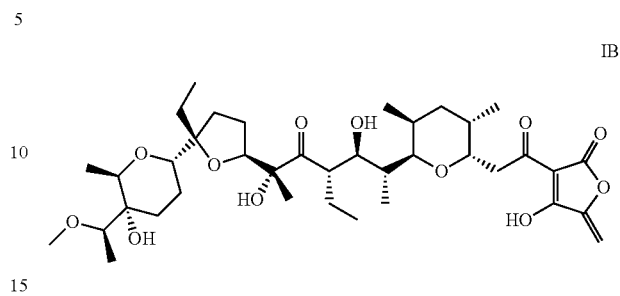

IB

Salts, including pharmaceutically acceptable salts of the disclosed compounds are within the scope of the present technology. When the compound of the present technology has an acidic group, such as for example, a carboxylic acid group or an enol group, it can form salts with metals, such as alkali and earth alkali metals (e.g. $Na^+$, $Li^+$, $K^+$, $Ca^{2+}$, $Zn^{2+}$), ammonia or organic amines (e.g. dicyclohexylamine, trimethylamine, triethylamine, pyridine, picoline, ethanolainine, diethanolamine, triethanolamine) or basic amino acids (e.g. arginine, lysine and ornithine). Such a salt can be prepared in situ during isolation and purification of ecteinamycin or by separately reacting the purified ecteinamycin in its free acid form with a suitable base, and isolating the salt thus formed.

While not wishing to be bound by theory, salts of ecteinamycin with bases are believed to form between the acidic 4-hydroxyl proton on the 5-methylenefuran-2-one ring and the base. The salts of any embodiment herein may be sodium, potassium, magnesium or silver salts. All salts isolated have been amorphous solids; no crystalline salts have been found.

In another aspect the present technology provides a pharmaceutical composition including any of the compounds described herein or a pharmaceutical salt thereof, and a pharmaceutically acceptable carrier. Pharmaceutical compositions of the present technology may be formulated for oral, parenteral, nasal, or topical administration.

Thus, the pharmaceutical composition may include a compound of Formula I, or pharmaceutically acceptable salt thereof, and a pharmaceutically acceptable carrier, wherein Formula I has the structure:

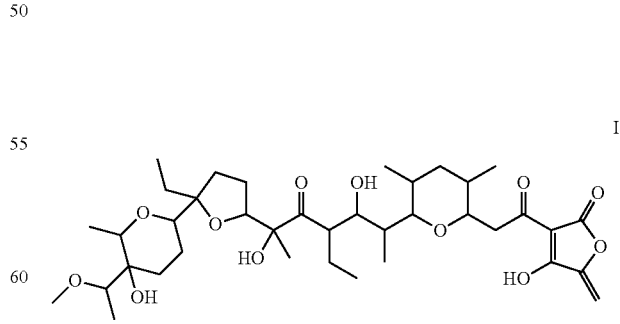

I

The pharmaceutical composition may include a compound of Formula IA or a pharmaceutically acceptable salt thereof, and a pharmaceutically acceptable carrier, wherein Formula IA has the structure:

IA

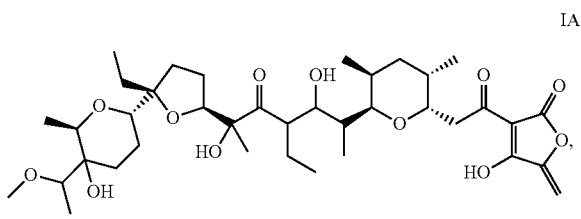 [SMILES: C=C1OC(=O)C(C(=O)C[C@@H]2O[C@@H](C(C)C(O)C(CC)C(=O)C(C)(O)[C@@H]3CC[C@@](CC)([C@@H]4CCC(O)(C(C)OC)[C@@H](C)O4)O3)[C@@H](C)C[C@@H]2C)=C1O]

As disclosed above, the compound of Formula IA may have the configuration at C15, C17, C18, C22, C33 and C36 as shown in at least one row of Table 1.

The pharmaceutical composition may include a compound of Formula IB or a pharmaceutically acceptable salt thereof, and a pharmaceutically acceptable carrier, wherein Formula IB has the structure:

IB

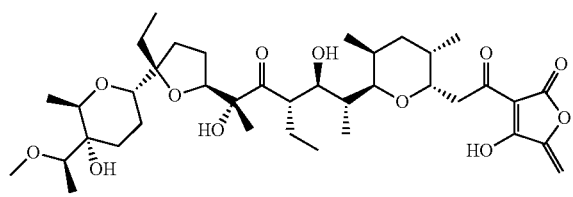

The pharmaceutical compositions of any embodiment herein may be formulated for oral, parenteral, nasal, or topical administration. In any embodiment herein, the pharmaceutical composition may include an effective amount of a compound of any embodiment of the present technology. The effective amount may be an effective amount for treating a bacterial infection. The effective amount may be an effective amount for treating a bacterial infection caused by one or more of *Clostridium, Staphylococcus*, and *Enterococcus*. For example, the effective amount may be an effective amount for treating a bacterial infection caused by one or more of *C. difficile, S. aureus*, methicillin-resistant *S. aureus*, vancomycin-resistant *Enterococcus, P. aeruginosa*, and *Kelbsiella pneumoniae*.

In an aspect, a method of disrupting ion transport in bacteria is provided, where the method includes contacting bacteria with an effective amount of any of the compounds described herein or a salt thereof, or any pharmaceutical composition described herein including any embodiment of the compounds of the present technology, with the bacteria, where the effective amount of the compound disrupts ion transport in the bacteria. The bacteria may include one or more of *Clostridium, Staphylococcus*, and *Enterococcus*. The bacteria may include one or both of *C. difficile* and *S. aureus*. The bacteria may include one or more of methicillin-resistant *S. aureus*, vancomycin-resistant *Enterococcus*, and *C. difficile*, and/or one or both of *P. aeruginosa* or *Kelbsiella pneumonia*. In the method, disrupting ion transport may include disrupting potassium ion transport. The contacting may include adding a solution that includes the compound or pharmaceutical composition to the bacteria. The effective amount may be an effective amount for disrupting the ion transport of bacteria in a subject. The effective amount may be an effective amount for disrupting the ion transport of bacteria in a culture.

In another aspect, the present technology provides a method of treating a bacterial infection comprising administering an effective amount of ecteinamycin, a salt thereof, or a pharmaceutical composition as described herein to a mammal in need thereof. The mammal may be, e.g., a human, primate (e.g. monkey, chimpanzee, ape), cat, dog, pig, mouse, rat, horse, sheep, among others. In any embodiment described herein, the mammal may be human. The infection may occur, e.g., in the throat, mouth, pharynx, esophagus, kidneys, bladder, lungs, brain, joints, heart, intestinal tract, skin and genitalia (including vagina and penis), or may be systemic, in, e.g., immunocompromised patients, sepsis. In any embodiment of the present methods, the bacterial infection may be caused by gram positive or gram negative bacteria. The bacterial infection may be caused by one or more of *Clostridium, Staphylococcus*, and *Enterococcus*. In any embodiment described herein, the bacterial infection may be caused by one or both of *C. difficile* and *S. aureus*. In any embodiment described herein, the bacterial infection may be caused by one or more of methicillin-resistant *S. aureus*, vancomycin-resistant *Enterococcus*, and *C. difficile*.

In yet another aspect the present technology provides ecteinamycin of any embodiment described herein (including the pharmaceutical compositions), for use in therapy, such as for treatment of bacterial infections. The encteinamycin is provided in an effective amount for treating the bacteria infection. In any embodiment, the bacterial infection may be caused by one or more of *Clostridium*, e.g., *C. difficile, Staphylococcus* (e.g., *S. aureus*), and *Enterococcus*. In any embodiment, the bacterial infection may be caused by one or more of methicillin-resistant *S. aureus*, vancomycin-resistant *Enterococcus*, and *C. difficile*. The bacteria may include one or both of *C. difficile* and *S. aureus*. The bacteria may include one or both of *P. aeruginosa* or *Kelbsiella pneumonia*. The present technology provides ecteinamycin of any embodiment described herein for use in the manufacture of a medicament for treating a bacterial infection. The bacterial infection may be caused by any one or more of the bacteria described herein.

In another aspect, the present technology provides pharmaceutical compositions of the herein-described compounds (including but not limited to compounds of Formula I, IA, and IB) with a second antibacterial agent, e.g., beta-lactams, protein synthesis inhibitors, as well as methods of using the same. Antibacterial agents include drugs which demonstrate clinical benefit in treatment of bacterial infections in a mammal, including a human. In any embodiment described herein, an effective amount of a compound as described herein (including but not limited to compounds of Formula I, IA, and IB), a salt thereof, or a pharmaceutical composition comprising the compound or salt thereof, and a pharmaceutically acceptable carrier, may be administered to a mammal in need thereof, wherein the second antibacterial agent is administered to the mammal in need thereof simultaneously, sequentially or separately with a compound as described herein, the salt thereof, or any embodiment of the pharmaceutical composition as describe herein. While not wishing to be bound by theory, it is believed that the compounds described herein produce their antibacterial activity by acting as ionophores.

The combination of a compound described herein and a second antibacterial agent may be synergistic and synergistically effective amounts of the compound and/or second agent may be used. That is, lower amounts of the compound and/or agent may be used than would be the case if the therapeutic effects of the compounds and/or agents were merely additive.

"Treating" within the context of the instant technology, means alleviation, in whole or in part, of symptoms associated with a disorder or disease, or slowing, inhibition or halting of further progression or worsening of those symptoms, or prevention or prophylaxis of the disease or disorder in a subject at risk for developing the disease or disorder. For example, within the context of treating bacterial infections, successful treatment may include reduction or eradication of the pathogenic bacteria, including gram positive or gram negative bacteria, from the body; clinical benefit; an alleviation of symptoms, such as a reduction or elimination of diarrhea, fever, abdominal pain, nausea, vomiting, respiratory compromise, joint swelling and tenderness, skin lesions, urinary tract symptoms (dysuria, frequency, flank pain).

As used herein, an "effective amount" of a compound of the present technology refers to an amount of the compound that alleviates, in whole or in part, symptoms associated with a disorder or disease, or slows or halts of further progression or worsening of those symptoms, or prevents or provides prophylaxis for the disease or disorder in a subject at risk for developing the disease or disorder. Those skilled in the art are readily able to determine an effective amount. For example, one way of assessing an effective amount for a particular disease state is by simply administering a compound of the present technology to a patient in increasing amounts until progression of the disease state is decreased or stopped. An "effective amount" of a compound of the present technology also refers to an amount of the compound that, for example, reduces a population of bacteria where the bacterial population may outside a subject (e.g., in a media in a container).

The instant technology also provides for compositions and medicaments including a compound disclosed herein and a pharmaceutically acceptable carrier. Such compositions may be prepared by mixing one or more compounds of the present technology, pharmaceutically acceptable salts thereof or stereoisomers thereof, with pharmaceutically acceptable carriers, excipients, binders, diluents or the like to treat bacterial infections. The compounds and compositions of the present technology may be used to prepare formulations and medicaments that treat a variety of bacterial infections, e.g., gram positive infections such as *Clostridium, Enterococcus,* and *Staphylococcus,* or gram negative infections such as *P. aeruginosa, Kelbsiella pneumoniae.* Such compositions can be in the form of, for example, granules, powders, tablets, capsules, creams, ointments, syrup, suppositories, injections, emulsions, elixirs, suspensions or solutions. The instant compositions can be formulated for various routes of administration, for example, by oral, parenteral, topical, injection, rectal, nasal, vaginal, or via implanted reservoir. Parenteral or systemic administration includes, but is not limited to, subcutaneous, intravenous, intraperitoneally, intramuscular, intrathecal, intracranial, and intracerebroventricular injections. The following dosage forms are given by way of example and should not be construed as limiting the instant technology.

For oral, buccal, and sublingual administration, powders, suspensions, granules, tablets, pills, capsules, gelcaps, and caplets are acceptable as solid dosage forms. These can be prepared, for example, by mixing one or more compounds disclosed herein, or pharmaceutically acceptable salts or stereoisomers thereof, with at least one additive such as a starch or other additive. Suitable additives are sucrose, lactose, cellulose sugar, mannitol, maltitol, dextran, starch, agar, alginates, chitins, chitosans, pectins, tragacanth gum, gum arabic, gelatins, collagens, casein, albumin, synthetic or semi-synthetic polymers or glycerides. Optionally, oral dosage forms can contain other ingredients to aid in administration, such as an inactive diluent, or lubricants such as magnesium stearate, or preservatives such as paraben or sorbic acid, or anti-oxidants such as ascorbic acid, tocopherol or cysteine, a disintegrating agent, binders, thickeners, buffers, sweeteners, flavoring agents or perfuming agents. Tablets and pills may be further treated with suitable coating materials known in the art.

Liquid dosage forms for oral administration may be in the form of pharmaceutically acceptable emulsions, syrups, elixirs, suspensions, and solutions, which may contain an inactive diluent, such as water. Pharmaceutical formulations and medicaments may be prepared as liquid suspensions or solutions using a sterile liquid, such as, but not limited to, an oil, water, an alcohol, and combinations of these. Pharmaceutically suitable surfactants, suspending agents, emulsifying agents, may be added for oral or parenteral administration.

As noted above, suspensions may include oils. Such oils include, but are not limited to, peanut oil, sesame oil, cottonseed oil, corn oil and olive oil. Suspension preparation may also contain esters of fatty acids such as ethyl oleate, isopropyl myristate, fatty acid glycerides and acetylated fatty acid glycerides. Suspension formulations may include alcohols, such as, but not limited to, ethanol, isopropyl alcohol, hexadecyl alcohol, glycerol and propylene glycol. Ethers, such as but not limited to, poly(ethyleneglycol), petroleum hydrocarbons such as mineral oil and petrolatum; and water may also be used in suspension formulations.

Injectable dosage forms generally include aqueous suspensions or oil suspensions, which may be prepared using a suitable dispersant or wetting agent and a suspending agent. Injectable forms may be in solution phase or in the form of a suspension, which is prepared with a solvent or diluent. Acceptable solvents or vehicles include sterilized water, Ringer's solution, or an isotonic aqueous saline solution. Alternatively, sterile oils may be employed as solvents or suspending agents. Typically, the oil or fatty acid is non-volatile, including natural or synthetic oils, fatty acids, mono-, di- or tri-glycerides.

For injection, the pharmaceutical formulation and/or medicament may be a powder suitable for reconstitution with an appropriate solution as described above. Examples of these include, but are not limited to, freeze dried, rotary dried or spray dried powders, amorphous powders, granules, precipitates, or particulates. For injection, the formulations may optionally contain stabilizers, pH modifiers, surfactants, bioavailability modifiers and combinations of these.

Compounds of the present technology also may be formulated as a composition for topical administration (e.g., vaginal cream). These formulations may contain various excipients known to those skilled in the art. Suitable excipients may include, but are not limited to, cetyl esters wax, cetyl alcohol, white wax, glyceryl monostearate, propylene glycol monostearate, methyl stearate, benzyl alcohol, sodium lauryl sulfate, glycerin, mineral oil, water, carbomer, ethyl alcohol, acrylate adhesives, polyisobutylene adhesives, and silicone adhesives.

The composition may be in the form of a vaginal cream containing the composition of matter as set forth herein present in a nonliquefying base. The nonliquefying base may contain various inactive ingredients such as, for example, cetyl esters wax, cetyl alcohol, white wax, glyceryl monostearate, propylene glycol monostearate, methyl stearate, benzyl alcohol, sodium lauryl sulfate, glycerin, and mineral oil. Such composition may be formulated similar to PREMARIN® Vaginal Cream made commercially available by Wyeth-Ayerst Laboratories.

Dosage units for rectal administration may be prepared in the form of suppositories which may contain the composition of matter in a mixture with a neutral fat base, or they may be prepared in the form of gelatin-rectal capsules which contain the active substance in a mixture with a vegetable oil or paraffin oil.

Compounds of the present technology may be administered to the lungs by inhalation through the nose or mouth. Suitable pharmaceutical formulations for inhalation include solutions, sprays, dry powders, or aerosols containing any appropriate solvents and optionally other compounds such as, but not limited to, stabilizers, antimicrobial agents, antioxidants, pH modifiers, surfactants, bioavailability modifiers and combinations of these. Formulations for inhalation administration contain as excipients, for example, lactose, polyoxyethylene-9-lauryl ether, glycocholate and deoxycholate. Aqueous and nonaqueous aerosols are typically used for delivery of inventive compounds by inhalation.

Ordinarily, an aqueous aerosol is made by formulating an aqueous solution or suspension of the compound together with conventional pharmaceutically acceptable carriers and stabilizers. The carriers and stabilizers vary with the requirements of the particular compound, but typically include nonionic surfactants (Tweens, Pluronics, or polyethylene glycol), innocuous proteins such as serum albumin, sorbitan esters, oleic acid, lecithin, amino acids such as glycine, buffers, salts, sugars or sugar alcohols. Aerosols generally are prepared from isotonic solutions. A nonaqueous suspension (e.g., in a fluorocarbon propellant) can also be used to deliver compounds of the present technology.

Aerosols containing compounds for use according to the present technology are conveniently delivered using an inhaler, atomizer, pressurized pack or a nebulizer and a suitable propellant, e.g., without limitation, pressurized dichlorodifluoromethane, trichlorofluoromethane, dichlorotetrafluoroethane, nitrogen, air, or carbon dioxide. In the case of a pressurized aerosol, the dosage unit may be controlled by providing a valve to deliver a metered amount. Capsules and cartridges of, for example, gelatin for use in an inhaler or insufflator may be formulated containing a powder mix of the compound and a suitable powder base such as lactose or starch. Delivery of aerosols of the present technology using sonic nebulizers is advantageous because nebulizers minimize exposure of the agent to shear, which can result in degradation of the compound.

For nasal administration, the pharmaceutical formulations and medicaments may be a spray, nasal drops or aerosol containing an appropriate solvent(s) and optionally other compounds such as, but not limited to, stabilizers, antimicrobial agents, antioxidants, pH modifiers, surfactants, bioavailability modifiers and combinations of these. For administration in the form of nasal drops, the compounds may be formulated in oily solutions or as a gel. For administration of nasal aerosol, any suitable propellant may be used including compressed air, nitrogen, carbon dioxide, or a hydrocarbon based low boiling solvent.

Besides those representative dosage forms described above, pharmaceutically acceptable excipients and carriers are generally known to those skilled in the art and are thus included in the instant present technology. Such excipients and carriers are described, for example, in "Remingtons Pharmaceutical Sciences" Mack Pub. Co., New Jersey (1991), which is incorporated herein by reference.

The formulations of the present technology may be designed to be short-acting, fast-releasing, long-acting, and sustained-releasing as described below. Thus, the pharmaceutical formulations may also be formulated for controlled release or for slow release.

The instant compositions may also comprise, for example, micelles or liposomes, or some other encapsulated form, or may be administered in an extended release form to provide a prolonged storage and/or delivery effect. Therefore, the pharmaceutical formulations and medicaments may be compressed into pellets or cylinders and implanted intramuscularly or subcutaneously as depot injections or as implants such as stents. Such implants may employ known inert materials such as silicones and biodegradable polymers.

Specific dosages may be adjusted depending on conditions of disease, the age, body weight, general health conditions, sex, and diet of the subject, dose intervals, administration routes, excretion rate, and combinations of drugs. Any of the above dosage forms containing effective amounts are well within the bounds of routine experimentation and therefore, well within the scope of the instant technology.

A therapeutically effective amount of a compound of the present technology may vary depending upon the route of administration and dosage form. Effective amounts of such compounds typically fall in the range of about 0.01 up to about 100 mg/kg/day, or about 0.05 to about 50 mg/kg/day, and more typically in the range of about 0.1 up to 5 mg/kg/day. Typically, the compound or compounds of the instant technology are selected to provide a formulation that exhibits a high therapeutic index. The therapeutic index is the dose ratio between toxic and therapeutic effects and can be expressed as the ratio between $LD_{50}$ and $ED_{50}$. The $LD_{50}$ is the dose lethal to 50% of the population and the $ED_{50}$ is the dose therapeutically effective in 50% of the population. The $LD_{50}$ and $ED_{50}$ are determined by standard pharmaceutical procedures in animal cell cultures or experimental animals.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

The present technology is further illustrated by the following examples, which should not be construed as limiting in any way.

EXAMPLES

General Experimental Procedures

Optical rotations were measured on a Perkin-Elmer 241 Polarimeter. UV spectra were recorded on an Aminco/OLIS UV-Vis Spectrophotometer. IR spectra were measured with a Bruker Equinox 55/S FT-IR Spectrophotometer. NMR spectra were obtained in $CDCl_3$ with a Bruker Avance 600 MHz spectrometer equipped with a 1.7 mm $^1H\{^{13}C/^{15}N\}$ cryoprobe and a Bruker Avance 500 MHz spectrometer equipped with a $^{13}C/^{15}N\{^1H\}$ cryoprobe. HRMS data were acquired with a Bruker MaXis 4G QTOF mass spectrometer. RP HPLC was performed using a Shimadzu Prominence HPLC system and a Phenomenex Luna C18 column (250× 10 mm, 5 µm).

Example 1: Isolation of Ecteinamycin from Bacteria Associated with Ascidiacea Biological Material.

Ascidian specimens were collected in the Florida Keys (24° 37.487', 81° 27.443'). Identification was confirmed by Shirley Parker-Nance. A voucher specimen (FLK10-5-3) for *Ecteinascidia turbinata* (Herdman, 1880) is housed at the University of Wisconsin-Madison. For cultivation, a sample of ascidian (1 $cm^3$) was rinsed with sterile seawater, macerated using a sterile pestle in a micro-centrifuge tube, and dilutions were made in sterile seawater, with vortexing between steps to separate bacteria from heavier tissues. Dilutions were separately plated on three media: ISP2, R2A, and M4. Each medium was supplemented with 50 μg/mL cycloheximide and 25 μg/mL nalidixic acid. Plates were incubated at 28° C. for at least 28 days.

Sequencing.

16S rDNA sequencing was conducted as previously described (Wyche, T. P.; Hou, Y.; Braun, D.; Cohen, H. C.; Xiong, M. P.; Bugni, T. S. *J. Org. Chem.* 2011, 76, 6542-6547). WMMB499 was identified as an *Actinomadura* sp. and demonstrated 99% sequence similarity to *Actinomadura* sp. 13679C (accession number EU741239). The 16S sequence for WMMB499 was deposited in GenBank (accession number JX101467).

Fermentation, Extraction, and Isolation.

Two 10 mL seed cultures (25×150 mm tubes) in medium ASW-A (20 g soluble starch, 10 g glucose, 5 g peptone, 5 g yeast extract, 5 g $CaCO_3$ per liter of artificial seawater) were inoculated with strain WMMB499 and shaken (200 RPM, 28° C.) for seven days. 250 mL baffled flasks containing ASW-A (12×50 mL) were inoculated with 1 mL seed culture and were incubated (200 RPM, 28° C.) for seven days. Two-liter flasks (6×500 mL) containing medium ASW-A with Diaion HP20 (4% by weight) were inoculated with 25 mL from the 50 mL culture and shaken (200 RPM, 28° C.) for seven days. Filtered HP20 and cells were washed with $H_2O$ and extracted with acetone. The acetone extract (3.2 g) was subjected to liquid-liquid partitioning using 30% aqueous MeOH and $CHCl_3$ (1:1). The $CHCl_3$-soluble partition (2.2 g) was fractionated by Sephadex LH20 column chromatography ($CHCl_3$: MeOH, 1:1). Fractions containing ecteinamycin were subjected to RP HPLC (75/25% to 100/0% MeOH-ammonium acetate 10 mM in 15 mins) using a Phenomenex Luna C18 column (250×10 mm, 5 μm) and yielded ecteinamcyin (1.0 mg, RT 13.5 min). For $^{13}C$ incorporation, the same procedure was used with two-liter flasks (2×500 mL) containing medium ASW-A ($U^{13}C$-glucose substituted for unlabeled glucose).

Example 2: Structure Elucidation

Analytical data were gathered for ecteinamycin, including optical rotation, IR, HRMS, and NMR spectra.

Ecteinamycin: white solid; $[\alpha]^{25}_D$+67 (c 0.08, MeOH); UV (MeOH) $\lambda_{max}$ (log ε) 200 (3.91), 250 (4.16), 299 (3.89) nm; IR (ATR) $v_{max}$ 1735, 1635, 1538, 1457, 1215 $cm^{-1}$; $^1H$ and $^{13}C$ NMR (See FIGS. 1-7); HRMS $[M+H]^+$ m/z 709.4141 (calc'd for $C_{38}H_{61}O_{12}$, 709.4158).

Figure 8:
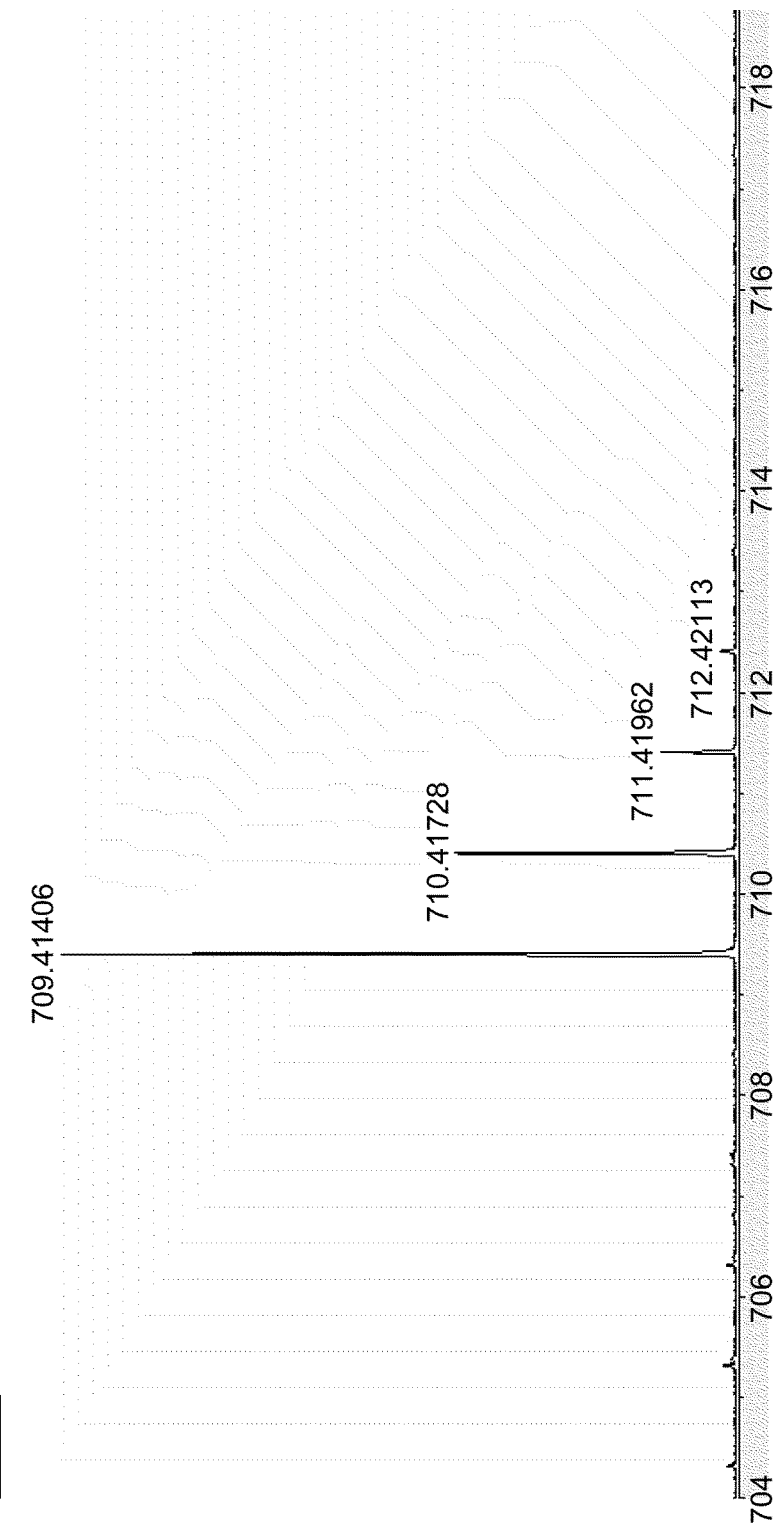
FIG. 8 shows a HRMS spectrum of ecteinamycin.
Figure 9A:
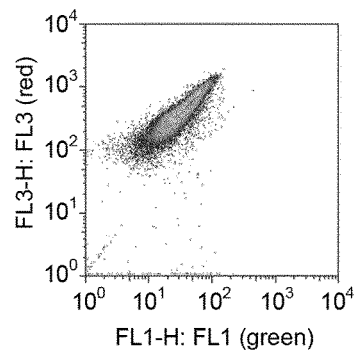
FIG. 9 Membrane depolarization assay. Flow cytometry analysis of MSSA cells treated with 3,3'-diethyloxacarbocyanine, iodide (DiOC$_2$(3)) dye control (9A), ecteinamycin (9B), and CCCP (9C).
FIG. 9D shows the ratio of red to green fluorescence for MSSA cells treated with DiOC$_2$(3) dye and corresponding compound.
Figure 9B:
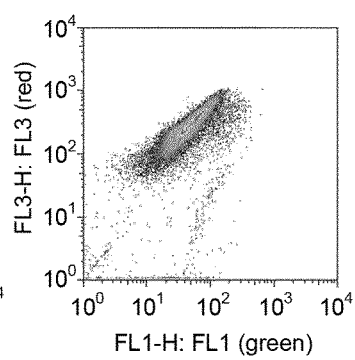
Figure 9C:
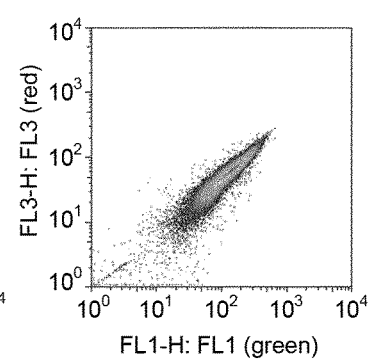
Figure 9D:
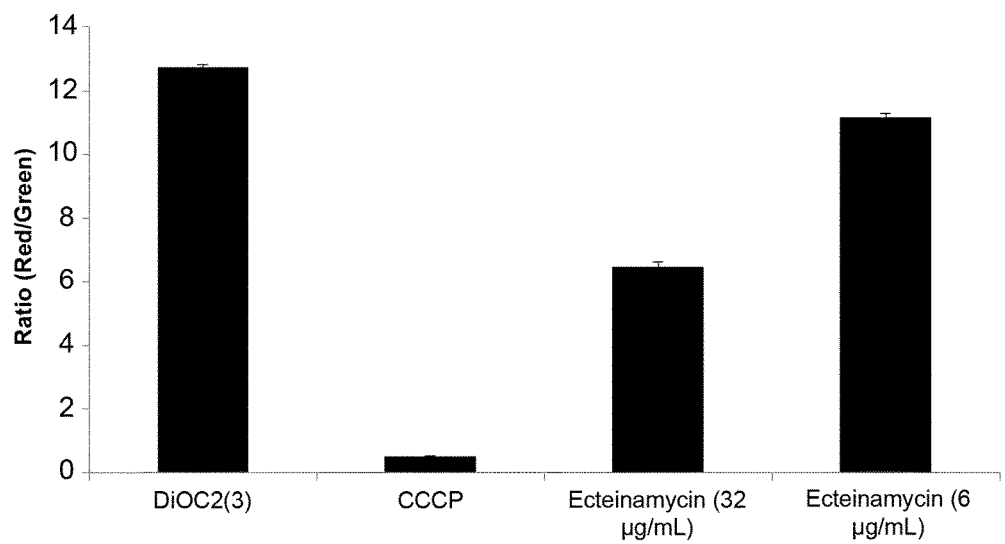

HRMS (FIG. 8) supported the molecular formula of $C_{38}H_{60}O_{12}$ for ecteinamycin (1). Extensive 1D and 2D NMR data (Table 4) allowed determination of the majority of the planar structure. $U^{13}C$-glucose was used to increase the incorporation of $^{13}C$ in the sample of ecteinamycin (1), and acquisition of a $^{13}C$-$^{13}C$ COSY provided the carbon backbone of the structure.

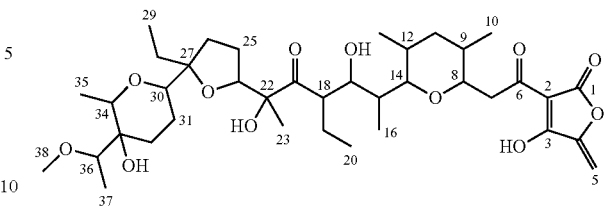

1

TABLE 4

$^1H$ and $^{13}C$ NMR data (600 MHz for $^1H$, 150 MHz for $^{13}C$, $CDCl_3$)

| Position | $\delta_C{}^b$ mult. | $\delta_H{}^a$ (J in Hz) | COSY | HMBC |
|---|---|---|---|---|
| 1 | 171.3, C | | | |
| 2 | 97.1, C | | | |
| 3 | 183.3, C | | | |
| 4 | 153.3, C | | | |
| 5 | 89.7, $CH_2$ | 5.16, s | | 2, 3, 4 |
|   |   | 4.77, s | | |
| 6 | 199.8, C | | | |
| 7 | 35.9, $CH_2$ | 3.46, d (11.6) | | 2, 3, 6, 8, 9 |
|   |   | 2.41, t (11.6) | | |
| 8 | 77.9, CH | 4.19, dd (11.6, 5.9) | 7, 9 | 6, 7, 9, 14 |
| 9 | 27.9, CH | 2.20, m | 10, 11 | 8, 10, 11 |
| 10 | 17.8, $CH_3$ | 0.95, d (6.8) | 9 | 8, 9, 11 |
| 11 | 36.5, $CH_2$ | 1.45, m | 9, 12 | |
| 12 | 29.1, CH | 1.76, m | 11, 13, 14 | |
| 13 | 11.3, $CH_3$ | 0.89, d (6.8) | 12 | 11, 12, 14 |
| 14 | 70.0, CH | 3.60, m | 12, 15 | 8, 11, 13, 17 |
| 15 | 36.7, CH | 1.50, m | 16 | 14, 16 |
| 16 | 7.5, $CH_3$ | 0.80, d (6.8) | 15 | 14, 15, 17 |
| 17 | 73.9, CH | 3.80, m | 18 | 14, 16, 18, 19 |
| 17-OH |   | 6.37, br s | 17 | 17, 18 |
| 18 | 49.0, CH | 3.60, m | 17, 19 | 17, 21 |
| 19 | 21.5, $CH_2$ | 1.59, m | 18, 20 | 21 |
|   |   | 1.28, m | | |
| 20 | 12.9, $CH_3$ | 0.72, t (7.2) | 19 | 18, 19 |
| 21 | 222.9, C | | | |
| 22 | 78.9, C | | | |
| 22-OH |   | 5.91, s | 23 | 21, 22, 23 |
| 23 | 20.7, $CH_3$ | 1.06, s | 22-OH | 21, 22, 24 |
| 24 | 84.1, CH | 4.43, dd (11.2, 6.4) | 25 | 22, 25, 26 |
| 25 | 75.0, $CH_2$ | 2.18, m | 24, 26 | |
|   |   | 1.84, m | | |
| 26 | 29.3, $CH_2$ | 1.74, m | 25 | 27, 28, 30 |
| 27 | 89.1, C | | | |
| 28 | 30.2, $CH_2$ | 1.64, m | 29 | 26, 27, 29, 30 |
|   |   | 1.40, m | | |
| 29 | 9.4, $CH_3$ | 0.77, t (7.5) | 28 | 27, 28 |
| 30 | 70.3, CH | 3.52, m | 31 | |
| 31 | 20.2, $CH_2$ | 1.94, m | 30 | 27 |
|   |   | 1.57, m | | |
| 32 | 25.0, $CH_2$ | 1.68, m | 33-OH | |
|   |   | 1.44, m | | |
| 33 | 73.2, C | | | |
| 33-OH |   | 4.39, s | 32 | 32, 33 |
| 34 | 74.9, CH | 3.98, q (6.4) | 35 | 30, 32, 33, 35 |
| 35 | 14.4, $CH_3$ | 1.11, d (6.4) | 34 | 33, 34 |
| 36 | 78.9, CH | 3.04, q (6.2) | 37 | 32, 34, 37, 38 |
| 37 | 11.3, $CH_3$ | 1.11, d (6.2) | 36 | 36 |
| 38 | 56.5, $CH_3$ | 3.26, s | | 36 |

A combination of ROESY correlations, coupling constants, $^{13}C$ chemical shifts, molecular modeling, and other spectroscopic methods were used to determine the relative configuration of ecteinamycin. A ROESY correlation between H-9 and H-13 suggested the C-10 and C-13 methyl groups were anti. C-10 and C-13 were assigned equatorial and axial, respectively, due to the $^{13}C$ chemical shifts. $^{13}C$ NMR shifts of equatorial carbons are further downfield (~17 ppm) than axial carbons (~11 ppm) in similar chemical systems. A ROESY correlation between H-7 and H-14 suggested that H-8 and H-14 were anti. A small coupling constant ($^3J_H$ 6.0 Hz) between H-8 and H-9 suggested that the two protons were cis. This relative configuration of H-8, H-9, H-12, and H-14 was confirmed by molecular modeling with Spartan10 software. The low energy conformer for each of the possible diastereomers for that cyclic system was modeled, and the proposed relative configuration (A) matched best with the experimental ROESY correlations and coupling constants.

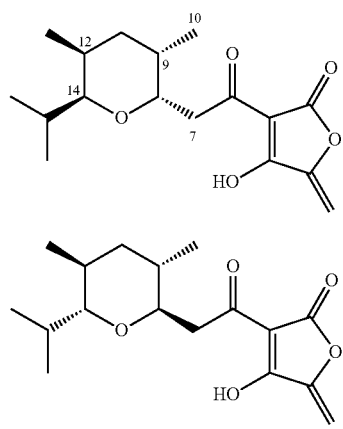

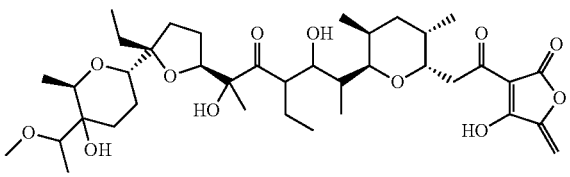 [SMILES: C=C1OC(=O)C(C(=O)C[C@@H]2O[C@@H](C(C)C(O)C(CC)C(=O)C(C)(O)[C@@H]3CC[C@@](CC)([C@@H]4CCC(O)(C(C)OC)[C@@H](C)O4)O3)[C@@H](C)C[C@@H]2C)=C1O]

A ROESY correlation between H-30 and H-35 suggested that H-30 and H-34 were anti. Although several other ROESY correlations existed within the C-24 to C-38 region, additional experiments were necessary in order to confidently assign the configuration for the remaining stereocenters. Considerable overlap in the upheld region of the 2D ROESY initially prevented assignment of ROESY correlations in this region. In order to clearly distinguish these correlations, a 1D selective TOCSY-NOESY NMR experiment was acquired. H-24 (4.43 ppm) was selectively excited and showed TOCSY correlations to several protons, including H-25a (2.18 ppm) and H-25b (1.84 ppm). The 1D selective TOCSY allowed for the isolation of these signals away from interfering signals in other portions of the structure. A 1D selective NOESY experiment was then completed by selecting exciting H-25a. Signals for H-23, H-25b, H-26, H-28b, and H-29 were seen in the 1D selective NOESY, indicating these protons were within 5 Å of H-25b. Most important of these signals were H-28b (1.40 ppm) and H-29 (0.77 ppm), which were across the ether ring. This data was compared to molecular models of the two possible isomers at C-24 and C-27. Spartan10 was used to calculate the low energy conformer for a truncated ecteinamycin with C-22 and C-28 syn and anti to each other. In the syn model, H-25a and H-25b were less than 5 Å from H-28a, H-28b, and H-29, in agreement with the ROESY NMR data. However, when C-22 and C-28 were anti to each other, H-25a was greater than 5 Å away from H-29 and thus, not matching the NOESY NMR data. Consequently, C-22 and C-28 were assigned syn to each other in the ether ring. The same procedure was repeated for a 1D selective NOESY of H-25b (1.84 ppm) and resulted in similar correlations.

After determining this relative configuration, considerable molecular modeling and DFT NMR calculations were undertaken in attempt to assign the configuration at the remaining stereocenters, but results at the time were inconclusive. Modified Mosher's method was attempted for the C-17 hydroxyl but did not form the expected product. Additionally, HSQMBC data were acquired on ecteinamycin in attempt to use the J-based configuration method to assign the stereochemistry for C-15 to C-18 but was inconclusive. Ecteinamycin was also compared to the structures of other polyether antibiotics. In particular, lasalocid and salinomycin have a very similar structural motif to ecteinamycin in the C-24 to C-38 region. Cane et al. proposed a stereochemical model that relates the stereochemistry for many of the polyether antibiotics, based partially on biosynthetic considerations. Many polyether antibiotics share certain similar structural features, and these compounds, in most cases, have the same stereochemistry in that region. Lasalocid and salinomycin have the exact same stereochemistry in the terminal ether ring, and while the model proposed by Cane et al. would suggest that ecteinamycin has the same stereochemistry, a comparison of $^1$H and $^{13}$C NMR data was inconclusive and prevented assigning the stereochemistry using this method.

Crystallization has been the primary method for determining the stereochemistry of polyether antibiotics. After considerable literature searches, the only other method used for determination of the absolute configuration of the polyether antibiotics has been total synthesis. Considerable efforts were undertaken to crystallize ecteinamycin, using a variety of solvents and conditions, but ultimately, no crystal was formed. Thus far, about half of the relative configuration of ecteinamycin has been assigned by the aforementioned NMR methods.

Example 2: Biological Activity of Ecteinamycin

In Vitro Assay.

Ecteinamycin was tested for antibacterial activity against *C. difficile* (ATCC BAA-1870), MRSA (ATCC #33591), MSSA (ATCC #29213), *E. coli* (ATCC #25922), *P. aeruginosa* (ATCC #27853), and VRE (ATCC), and MICs were determined using a dilution antimicrobial susceptibility test for aerobic (MRSA, MSSA, *E. coli*, *P. aeruginosa*, and VRE) and anaerobic (*C. difficile*) bacteria. Ecteinamycin was dissolved in DMSO, serially diluted to 10 concentrations (0.0313-32 µg/mL), and tested in a 96-well plate. Vancomycin was used as a control and exhibited an MIC of 1 µg/mL against MSSA and 1 µg/mL against MRSA. Ecteinamycin and vancomycin were tested in triplicate. Six untreated media controls were included on each plate. For MRSA, MSSA, *E. coli*, and *P. aeruginosa*, the plates were incubated at 33° C. for 18 h. For *C. difficile*, the plate was incubated at 36° C. for 48 h anaerobically and then read visually using a mirror apparatus. All manipulations to the plate were done inside the anaerobe chamber. The MIC was determined as the lowest concentration that inhibited visible growth.

Membrane Depolarization Assay.

*S. aureus* (ATCC #29213) cells were grown to log phase (14 h) in Mueller Hinton Broth cation-adjusted (MHB$_{50}$) and were diluted to 0.07 OD$_{600}$ with media. One mL aliquots were transferred to 1.5 mL centrifuge tubes and treated with the following in triplicate: 10 µL DMSO (control), 10 µL of 600 µg/mL ecteinamycin, 10 µL of 3.2 mg/mL ecteinamycin (1), 10 µL of 500 µM carbonyl cyanide m-chlorophenythydrazone (CCCP), and 10 µL of 3.2 mg/mL rifampicin. Additionally, each tube received 10 µL of 3 mM DiOC$_2$(3) (3,3'-diethyloxacarbocyanine iodide). The tubes were shaken for 15 minutes at room temperature. The cells were then analyzed with a FACSCalibur (BD Biosciences) flow cytometer and CellQuestPro software (BD Biosciences). Collected data represent the geometric means of fluorescence of 40,000 gated events.

Chemical Genomic Analysis.

A chemical genomic analysis of ecteinamycin was performed as described previously (Fling, S.-Y.; Sofiyev, V.; Schneiderman, J.; Hirschfeld, A. F.; Victor, R. E.; Woods, K.; Piotrowski, J. S.; Deshpande, R.; Li, S. C.; de Voogd, N. J.; Myers, C. L.; Boone, C.; Andersen, R. J.; Turvey, S. E. *ACS Chem. Biol.* 2014, 9, 247-257.). The optimal inhibitory concentration of ecteinamycin for chemical genomic profiling (70-80% growth versus solvent control in YP-Glucose media after 24 h of growth) was determined. A concentration of 250 µg/mL inhibited growth within this range. Two hundred µL cultures of a pooled, genome wide collection of *S. cerevisiae* deletion mutants with 250 µg/mL ecteinamycin or a DMSO control were grown in triplicate for 48 h at 30° C. The genomic DNA was extracted using the Epicentre MasterPure™ Yeast DNA purification kit. Mutant-specific molecular barcodes were amplified with specially designed multiplex primers containing adapters for Illumina sequencing. The barcodes were sequenced using an Illumina HiSeq2500 Rapid Run platform. Three replicates of each condition (ecteinamycin vs. DMSO) were sequenced. The barcode counts for each yeast deletion mutant in the presence of ecteinamycin were normalized against the DMSO control conditions to generate a Z-score to define sensitivity or resistance of individual strains (the chemical genomic profile). In addition, differential abundance analysis was calculated for each mutant's response to the ecteinamycin versus DMSO using edgeR. The mutants with very low counts (<5) were filtered out before using the edgeR package (version 3.4.2) to calculate an adjusted P-value and log fold change for each mutant. A Bonferroni corrected hypergeometric distribution test was used to search for significant enrichment of GO terms among the top sensitive and resistant deletion mutants with a P-value less than 0.0001.[42] The chemical genomic profile of ecteinamycin was compared against existing chemical genomic datasets by Pearson correlation.

Pharmacokinetic Analysis.

An Agilent 1100 LCMS system (ESI-MS positive mode) with a Phenomenex Kinetix C18 column (100×4.6 mm, 2.6 µm) at a flow rate of 0.5 mL/min was used for all analysis. The gradient was from 75% MeOH/25% 1 mM ammonium acetate in H$_2$O to 93% MeOH/7% 1 mM ammonium acetate in H$_2$O in 11 mins, then 93% MeOH/7% 1 mM ammonium acetate in H$_2$O to 100% MeOH for 0.1 min and holding 100% MeOH for 3.9 mins.

Assay Validation.

A standard curve was constructed using known concentrations of ecteinamycin (1000, 500, 250, 125, 62.50, 31.25, 15.625, 7.8125, 3.90625 ng/mL) in blank human plasma. Linear regression analysis was performed on the peak areas, and the resulting linear equation was used to calculate the ecteinamycin concentrations of quality control (QC) standards of ecteinamycin in human plasma (800, 200, 25, 12.5 ng/mL). The limit of detection was determined to be 31.25 ng/mL, and the limit of quantification was determined to be 62.50 ng/mL.

Animals.

Eight-to-nine-week-old FVB female mice weighing 20.5 to 25.6 g were used for all studies. Animals were maintained in accordance with the American Association for Accreditation of Laboratory Care criteria. Animal studies were approved by the University of Wisconsin Animal Care Committee.

Determination of Ecteinamycin in Plasma.

Ecteinamycin was formulated with polyethylene glycol (PEG) 300, 25 mM Tris (1:1), pH 8.9. Mice were treated orally at 5 mg/kg or by retro-orbital intravenous injection at 2.5 mg/kg. Retro-orbital intravenous injection at 5 mg/kg was lethal. After 30 mins and 1 h, approximately 400 µL of blood was collected from the chest cavity in BD microtainer tubes with lithium heparin. Blood was centrifuged at 10,000 rpm for 10 mins Fifty µL of supernatant was added to 200 µL of acetonitrile (containing 0.1% formic acid) in a new polypropylene tube, vortexed for 1 min, and centrifuged for 10 mins at 14,000 rpm at 4° C. One hundred µL was transferred to a 96 well polypropylene microplate, 100 µL of H$_2$O was added, and the plate was covered and shaken for 1 min and placed in the autosampler for analysis. Three replicates were completed for each time point for both oral and IV dosing (except 2 replicates for retro-orbital IV 1 h time point due to lethal injection of one mouse). Sample quantitation was determined by weighted ($R^2$) linear regression using a 9-point curve. Linear regression analysis was performed on the peak areas, and the resulting linear equation was used to calculate the ecteinamycin concentrations of the unknowns. The % oral bioavailability was calculated from the concentration of ecteinamycin (adjusted for dose) in plasma between oral and IV dose: [ecteinamycin$_{oral}$]/[ecteinamycin$_{IV}$]×100.

Biological Activity and Mechanism of Action

Ecteinamycin was screened against a panel of gram-positive and gram-negative bacteria. The minimum inhibitory concentration (MIC) of ecteinamycin is reported in Table 5. Ecteinamycin was particularly potent against gram-positive bacteria, which is consistent with the activity of ionophore antibiotics. Among gram-positive bacteria, ecteinamycin demonstrated selective inhibition of *C. difficile* with an MIC of ≤31 ng/mL. Nigericin, a polyether ionophore antibiotic, has also been reported to be selectively potent against *C. difficile* with an MIC of 2.5 ng/mL; monensin was not as potent with an MIC of 0.5 µg/mL against *C. difficile*.

TABLE 5

Minimum inhibitory concentration (MIC) of ecteinamycin

| Organism | MIC (µg/mL) |
| --- | --- |
| *E. coli* | 16 |
| Methicillin-sensitive *Staphylococcus aureus* | 0.125 |
| Methicillin-resistant *Staphylococcus aureus* | 0.125 |
| Vancomycin-resistant *Enterococcus* | 0.25 |
| *P. aeruginosa* | 8 |
| *S. cerevisiae* | 8 |
| *C. difficile* | ≤0.0313 |

Flow cytometry was used to determine if ecteinamycin, like other polyether ionophore antibiotics, depolarizes cell membranes. 3,3'-diethyloxacarbocyanine iodide ("$DiOC_2$(3)") fluoresces green in bacterial cells but shifts to red when the cell membrane is depolarized. Therefore, the ratio of red to green fluorescence is indicative of the membrane potential. *S. aureus* ATCC 92113 cells were treated with ecteinamycin at concentrations of 6 and 32 µg/mL.

Additionally, carbonyl cyanide m-chlorophenylhydrazone (CCCP), which has been demonstrated to depolarize cell membranes, was used as a positive control. All cells except the DMSO negative control were treated with $DiOC_2(3)$ and analyzed by flow cytometry. As shown in FIG. 9A-D, ecteinamycin demonstrated membrane depolarization of *S. aureus* cells at 6 µg/mL. CCCP demonstrated membrane depolarization to a greater extent than ecteinamycin. This mechanism of action therefore matches that of other ionophore antibiotics.

In parallel, chemical genomic profiling with the yeast, *Saccharomyces cerevisiae*, was used to investigate the mechanism of action of ecteinamycin. This method has been used for determining the mechanism of action and molecular target for many bioactive compounds, including natural products. Ecteinamcyin was screened against over four thousand deletion mutant yeast strains, genomic DNA was extracted, and mutant-specific DNA barcodes were amplified and sequenced by Illumina sequencing. Ecteinamycin sensitive and resistant mutants were determined by quantification of DNA-barcodes, providing a chemical genomic profile, which was used to evaluate the mechanism of action.

Ecteinamycin gave a distinct chemical genomic profile at 250 µg/mL (Table 6). When comparing the chemical genomic profile of ecteinamycin to an existing dataset of known compounds, the top two correlations were found to be with the polyether antibiotics duamycin and nigericin ($P<0.0001$). Both of these compounds act by generating ion channels in cellular membranes and inhibit golgi function in eukaryotic cells. The top sensitive mutant strains ($P<0.0001$) were significantly enriched for genes involved in post-golgi mediated transport ($P=9.1e^{-5}$). This enrichment was driven by sensitive mutants with deletions of the genes DRS2, APL4, APM2, and YPT7. No functional enrichment among the top mutant strains resistant to ecteinamycin was found. The most sensitive protein complex to ecteinamycin based on the sum of Z-scores of mutants in the complex, was the AP-1 adaptor complex, a membrane coat adaptor complex in the trans-golgi network. Only one significantly sensitive DAmP mutant ($P=0.03$) was identified, a hypomorph of SEC14, a phosphatidylinositol/phosphatidylcholine transfer protein required for correct trans-golgi network dynamics.

TABLE 6

Ecteinamycin responsive yeast deletion mutants. Fold change in abundance of the mutants relative to the solvent control was calculated with EdgeR. A fold change value <1 indicates sensitivity to ecteinamycin, while a value >1 indicates resistance.

| | Disrupted gene | Fold Change | Adj. P-value | Gene Function |
|---|---|---|---|---|
| Sensitive | PAR32 | 0.017 | $1.5e^{-39}$ | Putative protein of unknown function |
| | YMR010W | 0.122 | $3.13e^{-22}$ | Putative protein of unknown function |
| | YPT7 | 0.016 | $4.28e^{-22}$ | Rab family GTPase |
| | APL4 | 0.076 | $1.65e^{-21}$ | Gamma-adaptin; large subunit of the clathrin-associated protein (AP-1) complex |
| | APM2 | 0.037 | $3.11e^{-21}$ | homologous to the medium chain of mammalian clathrin-associated protein complex |
| | YOL162W | 0.145 | $8.75e^{-20}$ | Member of the Dal5p subfamily of the major facilitator family |
| | YPR089W | 0.110 | $1.83e^{-18}$ | Protein of unknown function; exhibits genetic interaction with ERG11 |
| | VPS38 | 0.087 | $8.25e^{-17}$ | Part of a Vps34p phosphatidylinositol 3-kinase complex |
| | TRP4 | 0.136 | $6.02e^{-16}$ | Anthranilate phosphoribosyl transferase; transferase of the tryptophan biosynthetic pathway |
| | DRS2 | 0.040 | $6.64e^{-16}$ | Trans-golgi network aminophospholipid translocase (flippase) |
| Resistant | PHO2 | 5.974 | $1.14e^{-22}$ | Homeobox transcription factor; regulatory targets include genes involved in phosphate metabolism |
| | UME6 | 10.979 | $2.56e^{-22}$ | Component of the Rpd3L histone deacetylase complex |
| | YPL205C | 4.953 | $6.57e^{-13}$ | Hypothetical protein; deletion of locus affects telomere length |
| | IRC25 | 3.732 | $1.23e^{-11}$ | Component of a heterodimeric Poc4p-Irc25p chaperone; involved in assembly of alpha subunits into the 20S proteasome |
| | MRH1 | 4.129 | $9.71e^{-11}$ | Protein that localizes primarily to the plasma membrane |
| | PRE9 | 5.995 | $3.46e^{-10}$ | Alpha 3 subunit of the 20S proteasome |
| | MSS11 | 2.585 | $7.36e^{-10}$ | Mitochondrial protein; forms a heterodimer complex with Mto1p that performs the 5-modification of the wobble uridine base in mitochondrial tRNAs |
| | EGT2 | 3.564 | $9.12e^{-10}$ | Glycosylphosphatidylinositol (GPI)-anchored cell wall endoglucanase |

TABLE 6-continued

Ecteinamycin responsive yeast deletion mutants. Fold change in abundance of the mutants relative to the solvent control was calculated with EdgeR. A fold change value <1 indicates sensitivity to ecteinamycin, while a value >1 indicates resistance.

| Disrupted gene | Fold Change | Adj. P-value | Gene Function |
|---|---|---|---|
| PHO84 | 2.986 | $4.7e^{-09}$ | High-affinity inorganic phosphate (Pi) transporter |
| HAL9 | 3.379 | $3.03e^{-08}$ | Putative transcription factor containing a zinc finger |

When the chemical genomic profile was compared to the genetic interaction network of *S. cerevisiae*, among the top 20 genetic mutant profiles there was significant enrichment for genes involved in the GO processes "regulation of intracellular pH" (P=0.007) driven by correlation with the genetic profiles of mutants of VMA8, VMA1, and VMA10. There was also significant enrichment for genes involved in "intra-golgi vesicle-mediated transport" (P=0.007) driven by correlation with the genetic profile of deletion mutant of COG6, COG8, COG5. Combined with the structural similarity of ecteinamycin and other polyether antibiotics, these data suggest ecteinamycin works through a similar mechanism by forming ion channels and disruption of golgi dynamics in eukaryotes.

Chemical genomic profiling was also performed in *Escherichia coli* to further investigate the mechanism of action of ecteinamycin. Similar to the chemical genomic profiling with yeast, ecteinamcyin was screened against over 6,000 deletion mutant *E. coli* strains, genomic DNA was extracted, and mutant-specific DNA barcodes were amplified and sequenced by Illumina sequencing. Ecteinamycin sensitive and resistant mutants were determined by quantification of DNA-barcodes in order to provide a chemical genomic profile to aid in evaluating the mechanism of action (Table 7).

The top 20 sensitive mutant strains were significantly enriched for genes involved in monovalent inorganic cation transport (P=0.05). This enrichment was driven by sensitive mutants with deletions of the genes atpA, atpF, trkA. TrkA encodes part of a $K^+$ transport system, suggesting ecteinomycin has a specificity towards transport of potassium ions.

TABLE 7

Ecteinamycin responsive *E. coli* deletion mutants. Fold change in abundance of the mutants relative to the solvent control was calculated with EdgeR. A fold change value <1 indicates sensitivity to ecteinamycin, while a value >1 indicates resistance.

| Disrupted gene | Fold Change | Adj. P-value | Gene Function |
|---|---|---|---|
| acrA | 0.087 | $2.59e^{-60}$ | AcrA membrane fusion protein |
| acrB | 0.189 | $3.60e^{-29}$ | AcrB RND-type permease |
| trkA | 0.145 | $4.19e^{-27}$ | NAD-binding component of TrK potassium transporter |
| sapD | 0.197 | $4.74e^{-21}$ | peptide ABC transporter SapABCDF - ATP binding subunit |
| csgE | 0.369 | $9.87e^{-20}$ | curli transport specificity factor |
| ldcA | 0.341 | $3.45e^{-18}$ | L,D-carboxypeptidase A |
| sapB | 0.241 | $1.28e^{-16}$ | peptide ABC transporter SapABCDF - membrane subunit |
| kdpD | 0.374 | $2.10e^{-15}$ | KdpD sensory histidine kinase |
| fis | 0.416 | $9.27e^{-15}$ | DNA-binding and bending protein |
| rpoS | 0.350 | $1.15e^{-13}$ | RNA polymerase, sigma S (sigma 38) factor |
| ycdR | 0.287 | $4.99e^{-13}$ | outer membrane lipoprotein |
| hupA | 0.518 | $1.37e^{-12}$ | transcriptional dual regulator HU-α (HU-2) |
| yhjK | 0.485 | $2.18e^{-12}$ | predicted diguanylate cyclase |
| atpA | 0.280 | $7.18e^{-12}$ | ATP synthase F1 complex - alpha subunit |
| yraP | 0.365 | $1.91e^{-11}$ | lipoprotein |
| dksA | 0.187 | $2.97e^{-11}$ | RNA polymerase-binding transcription factor DksA |
| atpF | 0.207 | $1.18e^{-10}$ | ATP synthase F0 complex - b subunit |

In addition, a pharmacokinetic study in mice was pursued to determine the oral bioavailability of ecteinamycin. A standard curve using known concentrations of ecteinamycin was constructed to determine the amount of ecteinamycin in the mouse plasma. Mice were dosed orally with ecteinamycin at 5 mg/kg, or by retro-orbital intravenous (IV) injection at 2.5 mg/kg. IV injection of ecteinamycin at 5 mg/kg was lethal so IV injection was reduced to 2.5 mg/kg. Accounting for this difference in dosage, the oral bioavailability was determined to be 10.9% after 30 mins of treatment and 29.3% after 1 h of treatment. These results are somewhat similar to other polyether ionophore antibiotics, such as salinomycin and monensin. Most animal studies for polyether ionophore antibiotics have focused on ruminant animals, such as cattle and chickens, which make up most of the market for anticoccidials. For example, oral bioavailability for monensin in chickens was determined to be 30%. Oral bioavailability of polyether ionophore antibiotics in ruminants does not usually exceed 50% as the compounds are rapidly metabolized in the liver. Additionally, toxicity issues exist for many of the polyether antibiotics at higher concentrations, similar to ecteinamycin.

EQUIVALENTS

The present disclosure is not to be limited in terms of the particular embodiments described in this application. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method of treating a bacterial infection comprising administering to a mammal in need thereof an effective amount of a compound of Formula I:

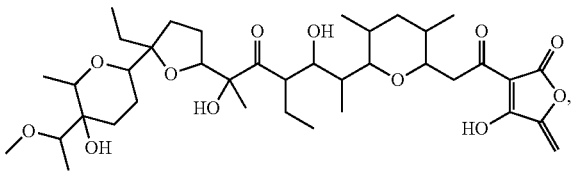

a salt thereof, or a pharmaceutical composition comprising the effective amount of the compound of Formula I or salt thereof and a pharmaceutically acceptable carrier, wherein the effective amount is effective for treating the bacterial infection in the mammal.

2. The method of claim 1, wherein the mammal is human.
3. The method of claim 1, wherein the bacterial infection is caused by one or more of *Clostridium, Staphylococcus*, and *Enterococcus*.
4. The method of claim 1, wherein the bacterial infection is caused by one or more of *C. difficile, S. aureus*, methicillin-resistant *S. aureus*, vancomycin-resistant *Enterococcus, P. aeruginosa*, and *Kelbsiella pneumonia*.
5. The method of claim 1, wherein a second antibiotic other than the compound of Formula I is administered to the mammal in need thereof simultaneously, sequentially or separately with the compound of Formula I, the salt thereof or the pharmaceutical composition.
6. The method of claim 5, wherein the second antibiotic is a beta-lactam or protein synthesis inhibitor.
7. A method of disrupting ion transport in bacteria, comprising contacting bacteria with an effective amount of a compound of Formula I:

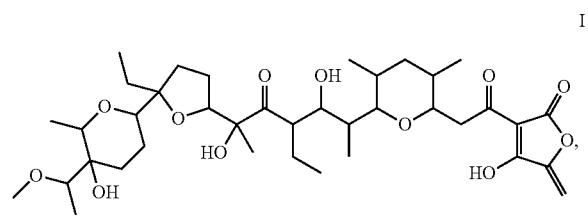 [SMILES: C=C1OC(=O)C(C(=O)CC2OC(C(C)C(O)C(CC)C(=O)C(C)(O)C3CCC(CC)(C4CCC(O)(C(C)OC)C(C)O4)O3)C(C)CC2C)=C1O]

a salt thereof, or with a pharmaceutical composition comprising the effective amount of the compound of Formula I or salt thereof and a pharmaceutically acceptable carrier, wherein the effective amount of the compound disrupts ion transport in the bacteria.

8. The method of claim 7, wherein the bacteria comprises one or more of *Clostridium, Staphylococcus,* and *Enterococcus*.
9. The method of claim 7, wherein the bacteria comprises one or more of *C. difficile, S. aureus*, methicillin-resistant *S. aureus*, vancomycin-resistant *Enterococcus, P. aeruginosa*, and *Kelbsiella pneumonia*.
10. The method of claim 7, wherein disrupting ion transport comprises disrupting potassium ion transport.
11. The method of claim 1, wherein the bacterial infection is caused by *Clostridium*.
12. The method of claim 1, wherein the bacterial infection is caused by *Staphylococcus*.
13. The method of claim 1, wherein the bacterial infection is caused by *Enterococcus*.
14. The method of claim 1, wherein the bacterial infection is caused by *C. difficile*.
15. The method of claim 1, wherein the bacterial infection is caused by *S. aureus*.
16. The method of claim 1, wherein the bacterial infection is caused by methicillin-resistant *S. aureus*.
17. The method of claim 1, wherein the bacterial infection is caused by vancomycin-resistant *Enterococcus*.
18. The method of claim 1, wherein the bacterial infection is caused by *P. aeruginosa*.
19. The method of claim 1, wherein the bacterial infection is caused by *Kelbsiella pneumonia*.

* * * * *